(12) United States Patent
Germanas

(10) Patent No.: US 12,357,552 B2
(45) Date of Patent: Jul. 15, 2025

(54) HYDROXYQUINOLINE COMPOUNDS AND METHODS OF USE AS PIGMENT MODIFYING AGENTS

(71) Applicant: Juris Germanas, Ellicot City, MD (US)

(72) Inventor: Juris Germanas, Ellicot City, MD (US)

(73) Assignee: Juris Germanas, Ellicott City, MD (US)

( * ) Notice: Subject to any disclaimer, the term of this patent is extended or adjusted under 35 U.S.C. 154(b) by 0 days.

(21) Appl. No.: 17/690,794

(22) Filed: Mar. 9, 2022

(65) Prior Publication Data

US 2022/0287941 A1    Sep. 15, 2022

Related U.S. Application Data

(60) Provisional application No. 63/158,517, filed on Mar. 9, 2021.

(51) Int. Cl.
| | | |
|---|---|---|
| *A61K 8/49* | (2006.01) | |
| *A61Q 17/04* | (2006.01) | |
| *A61Q 19/02* | (2006.01) | |
| *A61Q 19/10* | (2006.01) | |

(52) U.S. Cl.
CPC ............ *A61K 8/4926* (2013.01); *A61Q 17/04* (2013.01); *A61Q 19/02* (2013.01); *A61Q 19/10* (2013.01); *A61K 2800/28* (2013.01)

(58) Field of Classification Search
CPC .. A61K 8/4926; A61K 2800/28; A61K 31/47; A61K 45/06; A61K 2800/782; A61Q 17/04; A61Q 19/02; A61Q 19/10; A61P 17/02
See application file for complete search history.

(56) References Cited

U.S. PATENT DOCUMENTS

| | | | |
|---|---|---|---|
| 3,982,999 | A | 9/1976 | Kharasch |
| 6,005,006 | A | 12/1999 | Galey et al. |
| 8,729,097 | B2 | 5/2014 | Liu et al. |
| 2007/0166251 | A1* | 7/2007 | Dayan .................. A61K 8/891 424/62 |
| 2008/0146803 | A1 | 6/2008 | Lee et al. |
| 2008/0254130 | A1 | 10/2008 | Gupta |
| 2013/0296387 | A1 | 11/2013 | Saad |
| 2020/0170249 | A1* | 6/2020 | Polson .................. A61K 8/49 |
| 2020/0281853 | A1 | 9/2020 | Noe et al. |

FOREIGN PATENT DOCUMENTS

| | | |
|---|---|---|
| JP | 2019-502745 A | 1/2019 |
| WO | 2009067095 A1 | 5/2009 |
| WO | 2009140215 A2 | 11/2009 |
| WO | 2020/075158 A2 | 4/2020 |
| WO | 2020/263643 A1 | 12/2020 |

OTHER PUBLICATIONS

Netdoctor (netdoctor, betamethasone and clioquinol. 2013) (Year: 2013).*
Jacobsen et al. (Identifying Chelators for Metalloprotein Inhibitors Using a Fragment-Based Approach, J. Med. Chem. 2011 (Year: 2011).*
Searle (The selective depigmenting action of 8-hydroxyquinoline on hair growth in the mouse. Br. J. Derm. 1972 (Year: 1972).*
JAAD Liu; Research Letters, J Am Acad Dermol; vol. 85, No. 6, Dec. 2021, pp. 1608-1610.
JAAD Maymone; Research Letters, J Am Acad Dermatol, vol. 77, No. 4, (2017), pp. 775-778.
Silpa-Archa et al., Postinflammatory hyperpigmention: A comprehensive overview, Epidemiology, pathogenesis, clinical presentation, and noninvasive assessment technique, Continuing Medical Education, J Am Acad Dermatol, Oct. 2017, 15 pages.
Letter To The Editor "Remdesivir and chloroquine effectively inhibit the recently emerged novel coronavirus (2019-0nCoV) in vitro", Cell Research (2020), 30: pp. 269-271.
Germanas et al., "Discovery of small-molecule inhibitors of tyrosinase", Bioorangic & Medicinal Chemistry Letter 17 (2007) pp. 6871-6875.
Pillaiyar et al., "Skin whitening agents: mmedicinal chemistry perspective of tyrosinase inhibitors", Journal of Enzyme INhibition and Medicinal Chemistry, 2017, vol. 32, No. 1, pp. 403-425.
"Drug repurposing: progress, challenges and recommendations", Nature Reviews, Advance Online Publication, (2018) 18 pages.
Ismaya et al., "Crystal Structure of *Agaricus bisposus* Mushroom Tyrosinase: Identity of the Tetramer Subunits and Interaction with Tropolone", Biochemistry, 2011, pp. 5477-5686.
Lee et al., "Transcriptomic Repositioning Analysis Identifies mTOR Inhibitor as Potential Therapy for Epidermolysis Bullosa Simplex", Journal of Investigative Dermatology (2022), vol. 142, 8 pages.
Hah et al., "Induction of Melanogenesis by Rapamycin in Human MNT-1 Melanoma Cells", Ann Dermatol, vol. 24, No. 2, 2012, 7 pages.
Mann et al., "Inhibition of Human Tyrosinase Requires Molecular Motifs Distinctively Different from Mushroom Tyrosinase", JID Open, (2018), 8 pages.
Hornyak, "Next Time, Save Mushrooms for the Pizza!", Journal of Investigative Dermatology (2018, vol. 138, pp. 1470-1472.
Prachayasittikul et al., "8-Hydroxyquinolines: a review of their metal chelating properties and medicinal applications", Drug Design, Development and Therapy, Oct. 3, 2013, 22 pages.
Germanas et al., "Toward New Depigmenting Agents through Repurposing Existing Drugs: Substituted Hydroxyquinolines as Melanogenesis Inhibitors" 2022, The Authors. Published by Elsevier, Inc. on behalf of the Society for Investigative Dermatology, 18 pages.

(Continued)

*Primary Examiner* — Robert A Wax
*Assistant Examiner* — John Seungjai Kwon
(74) *Attorney, Agent, or Firm* — Edell, Shapiro & Finnan, LLC

(57) ABSTRACT

Embodiments disclosed provide pharmaceutical formulations for tyrosinase inhibitors, as well as methods for dermatological treatment of hyperpigmentation disorders. The pharmaceutical formulations comprise tyrosinase inhibitors, each containing a structural core of 8-hydroxyquinoline, and are applied in a suitable carrier as topical treatments for hyperpigmentation. In some embodiments at least one additional dermatologically active compound is present in the pharmaceutical formulation.

12 Claims, 13 Drawing Sheets

(56) References Cited

OTHER PUBLICATIONS

Int'l Search Report and Written Opinion n corresponding International Patent Application No. PCT/US22/19530, mailed Jul. 20, 2022.
International Preliminary Report on Patentability in PCT/US2022/019530, Sep. 12, 2023, 7 pages.
Germanas, J. et al., "Toward New Depigmenting Agents through Repurposing Existing Drugs: Substituted Hydroxyquinolines as Melanogenesis Inhibitors", Letter to the Editor, Journal of Investigative Dermatology, vol. 143(1), Jan. 2023 pp. 176-179.e2.
Germanas, J. et al., "Toward New Depigmenting Agents Through Repurposing: Hydroxyquinolines as Melanogenesis Inhibitors", AAD Presentation, 2021, 5 pages.
Ansar, M. et al., "A homozygous missense variant in type I keratin KRT25 causes autosomal recessive woolly hair", J Med Genet, vol. 52(10), Oct. 2015, pp. 1-10.
Bray, D. et al., "Complete Structure of an Epithelial Keratin Dimer: Implications for Intermediate Filament Assembly", PLoS One, vol. 10(7), Jul. 2015, pp. 1-22.
Chamcheu, J. et al., "Keratin Gene Mutations in Disorders of Human Skin and its Appendages", Arch Biochem Biophys., vol. 508(2), Apr. 2011, pp. 1-30.
Duverger, O. et al., "Hair keratin mutations in tooth enamel increase dental decay risk", The Journal of Clinical Investigation, vol. 124(12), Dec. 2014, pp. 5219-5224.
Fujimoto, A. et al., "A Missense Mutation within the Helix Initiation Motif of the Keratin K71 Gene Underlies Autosomal Dominant Woolly Hair/Hypotrichosis", Journal of Investigative Dermatology, vol. 132(10), Oct. 2012, pp. 2342-2349.
Langbein, L. et al., "K25 (K25irs1), K26 (K25irs2), K27 (K25irs3), and K28 (K25irs4) Represent the Type I Inner Root Sheath Keratins of the Human Hair Follicle", Journal of Investigative Dermatology, vol. 125(11), Nov. 2006, pp. 2377-2386.
Morgenthaler, C. et al., "A missense variant in the coil1A domain of the keratin 25 gene is associated with the dominant curly hair coat trait (Crd) in horse", Genetics Selection Evolutions, vol. 49(85), Nov. 2017, pp. 1-10.
Orchard, S. et al., "The MIntAct project-IntAct as a common curation platform for 11 molecular interaction databases", Nucleic Acids Research, vol. 42(Database issue), 2014, pp. D358-D363.
Shimomura, Y. et al., "Autosomal recessive woolly hair with hypotrichosis caused by a novel homozygous mutation in the P2RY5 gene", Exp Dermatol., vol. 18(3), Mar. 2009, pp. 1-9.
Shimomura, Y. et al., "Mutations in the LIPH gene in three Japanese families with autosomal recessive woolly hair/hypotrichosis", J Dermatol Sci., vol. 56(3), Dec. 2009, pp. 1-6.
Stenn, K. S. et al., "Controls of Hair Follicle Cycling", Physiological Reviews, vol. 81(1), Jan. 2001, pp. 449-494.
Tanaka, S. et al., "Mutations in the helix termination motif of mouse type I IRS keratin genes impair the assembly of keratin intermediate filament", Genomics, vol. 90(6), Dec. 2007, pp. 703-711.
Thomer, A. et al., "An epistatic effect of KRT25 on SP6 is involved in curly coat in horses", Scientific Reports, vol. 8 (6374), 2018, pp. 1-12.
Zernov, N. et al., "Autosomal Recessive Hypotrichosis with Woolly Hair Caused by a Mutation in the Keratin 25 Gene Expressed in Hair Follicles", Journal of Investigative Dermatology, vol. 136(6), Jun. 2016, pp. 1097-1105.
Cho, H. G. et al., "Identification of alpha-adrenergic agonists as potential therapeutic agents for dermatomyositis through drug-repurposing using public expression datasets", Journal of Investigative Dermatology, vol. 136(7), Jul. 2016, pp. 1-6.
Espin, J. et al., "Kinetic characterization of the substrate specificity and mechanism of mushroom tyrosinase", European Journal of Biochemistry, vol. 267(5), Mar. 2005, pp. 1270-1279.
Ebanks, J. et al., "Mechanisms Regulating Skin Pigmentation: The Rise and Fall of Complexion Coloration", International Journal of Molecular Sciences, vol. 10(9), Sep. 2009, pp. 4066-4087.
Hearing, V. et al., "Enzymatic control of pigmentation in mammals", FASEB Journal, vol. 5(15), Nov. 1991, pp. 2902-2909.

Lee, S.Y. et al., "Natural, semisynthetic and synthetic tyrosinase inhibitors", Journal of Enzyme Inhibition and Medicinal Chemistry, vol. 31(1), 2016, pp. 1-13.
Packianathan, N. et al., "Skin Care with Herbal Exfoliants", Functional Plant Science and Biotechnology, vol. 5 (Special Issue 1), 2010, pp. 94-97.
Pillaiyar, T. et al., "Inhibitors of melanogenesis: a patent review (2009-2014)" Expert Opin. Ther. Pat. vol. 25(7), Jul. 2015, pp. 1-14.
Sheth, V. et al., "Melasma: A comprehensive update: Part I" Journal of the American Academy of Dermatology, Continuing Medical Education, vol. 65(4), Oct. 2011, pp. 689-697.
Sheth, V. et al., "Melasma: A comprehensive update: Part II" Journal of the American Academy of Dermatology, Continuing Medical Education, vol. 65(4), Oct. 2011, pp. 699-714.
Winder, A. et al., "New assays for the tyrosine hydroxylase and dopa oxidase activities of tyrosinase", Eur J Biochem. vol. 198(2), Jun. 1991, pp. 317-326.
Zolghadri, S. et al., "A comprehensive review on tyrosinase inhibitors", Journal of Enzyme Inhibition and Medicinal Chemistry, vol. 34(1), 2019, pp. 279-309.
Smith, T. et al., "Three-dimensional modelling of interchain sequence similarities and differences in the coiled-coil segments of keratin intermediate filament heterodimers highlight features important in assembly", Journal of Structural Biology, vol. 162(1), Apr. 2008, pp. 139-151.
Khan, S. et al., "Mutations in the LPAR6 and LIPH genes underlie autosomal recessive hypotrichosis/woolly hair in 17 consanguineous families from Pakistan", Clinical and Experimental Dermatology, vol. 36(6), Aug. 2011, pp. 652-654.
Gu, LH. et al., "Keratin function in skin epithelia: a broadening palette with surprising shades", Current Opinion in Cell Biology, vol. 19(1), Feb. 2007, pp. 13-23.
Lachowicz, J. et al., "Metal coordination and tyrosinase inhibition studies with Kojic-βAla-Kojic", Journal of Inorganic Biochemistry, vol. 151, Oct. 2015, pp. 1-8.
Germanas, J. et al., "Toward New Depigmenting Agents through Repurposing Existing Drugs: Potent Tyrosinase Inhibitors with Novel Mechanisms of Action", Department of Dermatology, University of Maryland School of Medicine, Maryland Dermatology Associates.
Westerhof, W. et al., "Hydroquinone and its analogues in dermatology—a potential health risk", Journal of Cosmetic Dermatology, vol. 4(2), 2005 pp. 55-59.
Chang, T. "An Updated Review of Tyrosinase Inhibitors", International Journal of Molecular Sciences, vol. 10(6), Jun. 2009, pp. 2440-2475.
Food and Drug Administration, "Skin Bleaching Drug Products For Over-the-Counter Human Use; Proposed Rule", Federal Register, vol. 71(167), Aug. 29, 2006, pp. 51146-51155.
Sun, W. et al., "On the interpretation of tyrosinase inhibition kinetics", Journal of Enzyme Inhibition and Medical Chemistry, vol. 29(1), 2014, pp. 92-99.
Ito, S. et al., "Tyrosinase-catalyzed oxidation of rhododendrol produces 2-methylchromane-6,7-dione, the putative ultimate toxic metabolite: implications for melanocyte toxicity", Pigment Cell Melanoma Research, vol. 27(5), Sep. 2014, pp. 744-753.
Rohde, W. et al., "Hydroxyquinolines Inhibit Ribonucleic Acid-Dependent Deoxyribonucleic Acid Polymerase and Inactivate Rous Sarcoma Virus and Herpes Simplex Virus", Antimicrobial Agents and Chemotherapy, vol. 10(2), Aug. 1976, pp. 234-240.
Draelos, Z. "Skin lightening preparations and the hydroquinone controversy", Dermatologic Therapy, vol. 20(5), 2007, pp. 308-313.
Gershon, H. "Antifungal activity of bischelates of 5-,7-, and 5,7-halogenated 8-quinolinols with copper(II). Determination of appropriate dimensions of the long and short axes of the pores in the fungal spore wall", Journal of Medicinal Chemistry, vol. 17(8), Aug. 1974, pp. 824-827.
Khatib, S. et al., "Chalcones as potent tyrosinase inhibitors: the importance of a 2,4-substituted resorcinol moiety", Bioorganic & Medicinal Chemistry, vol. 13(2), Jan. 2005, 9 pages.
Downie, J. et al., "New OTC Topicals Target Hyperpigmentation, Melasma", Aesthetics Management in Association with Cosmetic Surgery Forum, Practical Dermatology, Mar. 2019, pp. 58-59.

(56) References Cited

OTHER PUBLICATIONS

"Drugs and Supplements Clioquinol (Topical Route)", Mayo Clinic, Feb. 1, 2024, 1 page.
E. Fougera & Co. a division of Fougera Pharmaceuticals Inc. "Betamethasone Valerate- betamethasone valerate cream; Betamethasone Valerate- betamethasone valerate ointment; Betamethasone Valerate- betamethasone valerate lotion" Dec. 2021, 14 pages.
Communication Pursuant to Rules 161(2) and 162 EPC dated Nov. 2, 2023 in corresponding EP Application No. 22767887.7, 3 pages.
Urey, J. et al., "Effects of EDTA on tyrosinase and L-amino-acid oxidase induction in Neurospora crassa", Biochimica et Biophysica Acta (BBA)—Enzymology, vol. 132(2), Mar. 15, 1967, pp. 300-309.
Palumbo, A. et al., "Mechanism of inhibition of melanogenesis by hydroquinone", Biochimica et Biophysica Acta, vol. 1073(1), Jan. 1991, pp. 85-90.
Paus, R. et al., "Human Hair Graying Revisited: Principles, Misconceptions, and Key Research Frontiers", Journal of Investigative Dermatology, vol. 144(3), Mar. 2024, pp. 474-491.
Mann, T. et al., "Inhibition of Human Tyrosinase Requires Molecular Motifs Distinctively Different from Mushroom Tyrosinase", Journal of Investigative Dermatology, vol. 138(7), Jul. 2018, pp. 1601-1608.
Curtis, A. et al., "Temporal Variations of Skin Pigmentation in C57Bl/6 Mice Affect Optical Bioluminescence Quantitation", Molecular Imaging and Biology, vol. 13(11), 2011, pp. 1114-1123.
"Betamethasone and clioquinol cream and ointment", netdoctor, Medicines > Skin and Hair, Jun. 2013, 7 pages.
The Jackson Laboratory's description of the B6 albino mouse strain, jax.org/strain/000058#, Retrieved Aug. 13, 2024, 1 page.
Sanchez-Ferrer, A. et al., "Tyrosinase: a comprehensive review of its mechanism", Biochimica et Biophysics Acta 1247, 1995, pp. 1-11.
The Extended European Search Report including the Supplementary European Search Report and the European Search Opinion for European Application No. 22767887.7 dated Feb. 4, 2025, 17 pages.
EP Communication pursuant to Rules 70(2) and 70a(2) EPC for European Application No. 22767887.7 dated Feb. 21, 2025, 1 page.
Rizk, M. et al., "LC of pharmaceutically important halogenated 8-hydroxyquinolines after precolumn derivatization with Pd (II)", Journal of Pharmaceutical and Biomedical Analysis, vol. 27(5), Feb. 2002, pp. 803-820.
Wojtowicz, E., "Reverse-Phase High-Performance Liquid Chromatographic Determination of Halogenated 8-Hydroxyquinoline Compounds in Pharmaceuticals and Bulk Drugs", Journal of Pharmaceutical Sciences, vol. 73(10), Oct. 1984, pp. 1430-1433.
Neldner, K., "The Hailogenated 8-HYDROXYQUINOLINES", International Journal of Dermatology, vol. 16(4), May 1977, pp. 267-273.
Joshi, S. K. et al., "Broxyquinoline .And Brobenzoxaldine in the Treatment of Trichomonal and Monilial Vaginitis", Journal of Obstetrics and Gynaecology of India, Aug. 1967, pp. 434-440.
Dlova, N. et al., "Skin-lightening creams used in Durban, South Africa", International Journal of Dermatology, vol. 51 (Suppl. 1), Nov. 2012, pp. 51-53.

\* cited by examiner

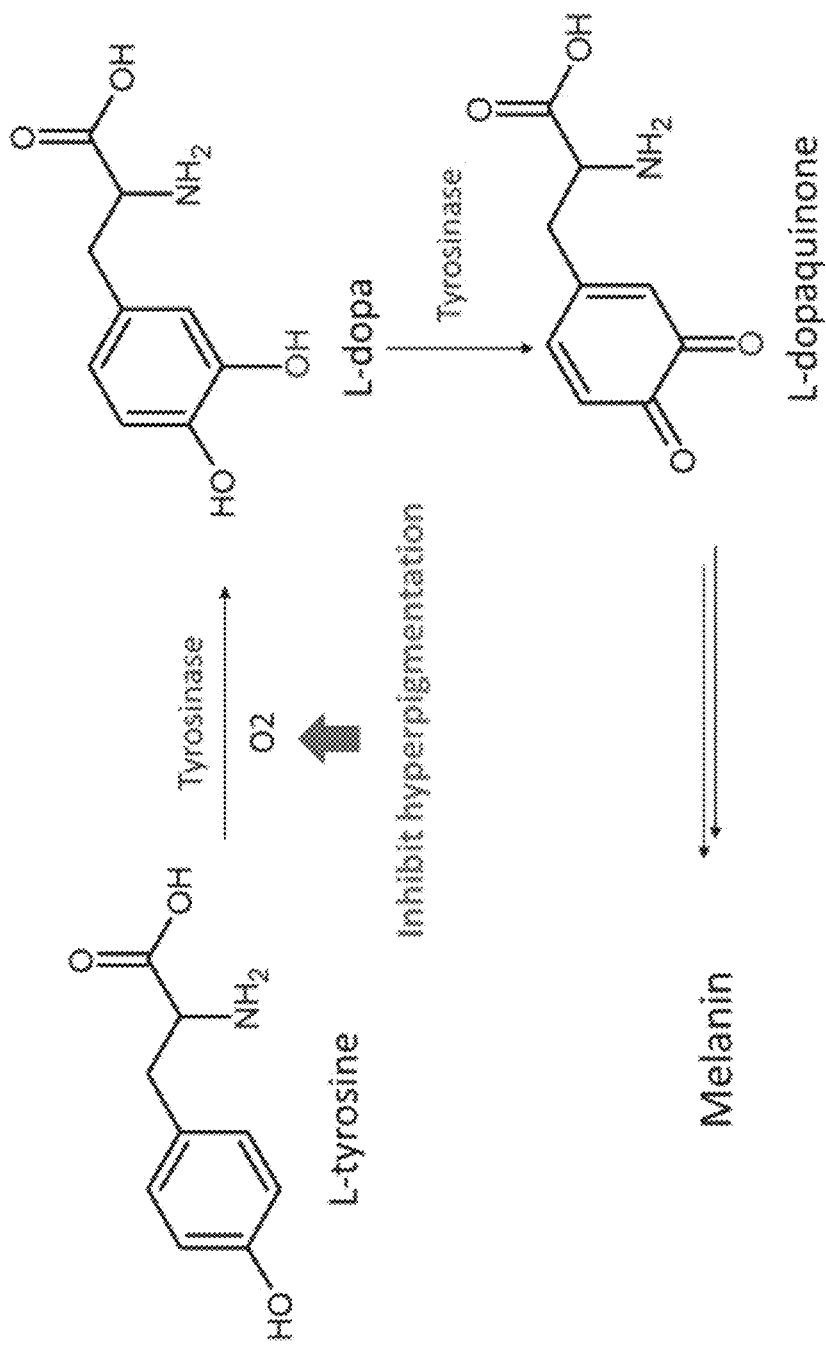
FIG. 1. The first steps in melanin synthesis in melanocytes. Inhibition of tyrosinase activity reduces hyperpigmentation.

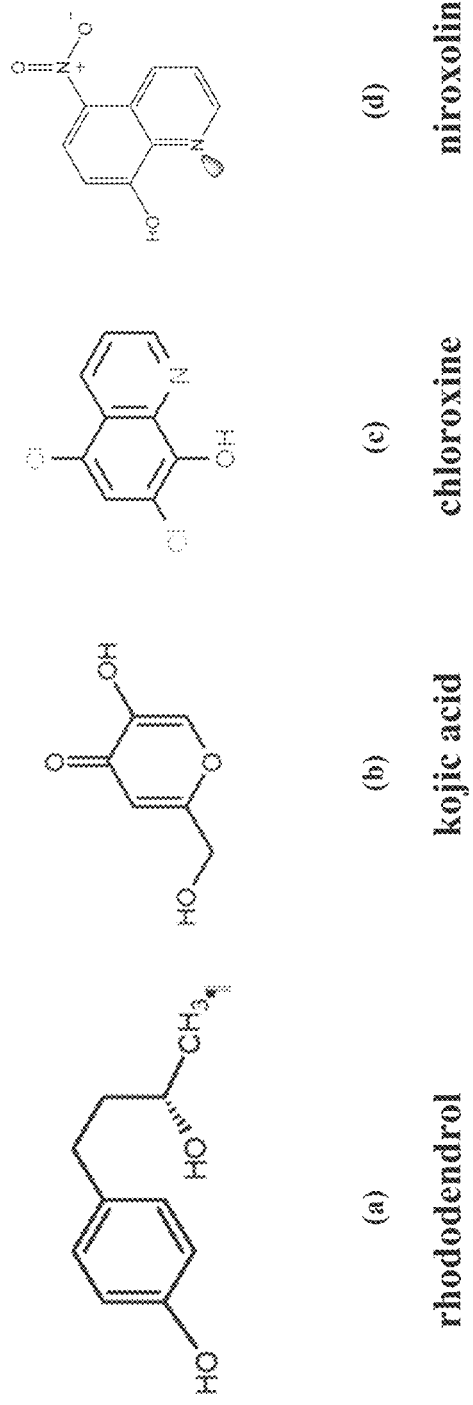
FIG. 2 (a) – (d). Structures of (a) rhododendrol, (b) kojic acid, (c) chloroxine, and (d) nitroxoline.

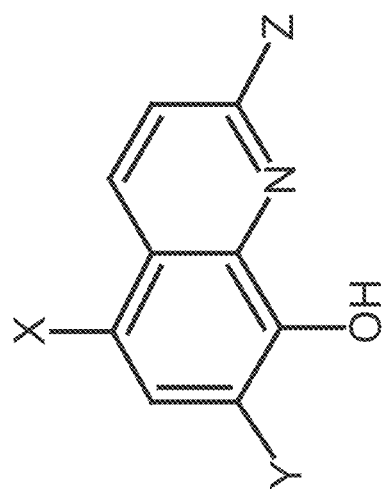
FIG. 3 (a). Hydroxyquinoline structures and their inhibition constant values
| X | Y | Z | Name | Ki (µM) | logP |
|---|---|---|---|---|---|
| NO₂ | H | H | Nitroxoline (1) | 0.9 | 0.79 |
| Cl | Cl | H | Chloroxine (2) | 12 | 1.736 |
| Cl | I | H | Clioquinol (3) | 367 | 2.182 |
| I | I | H | Iodoquinol (4) | 1290 | 2.628 |

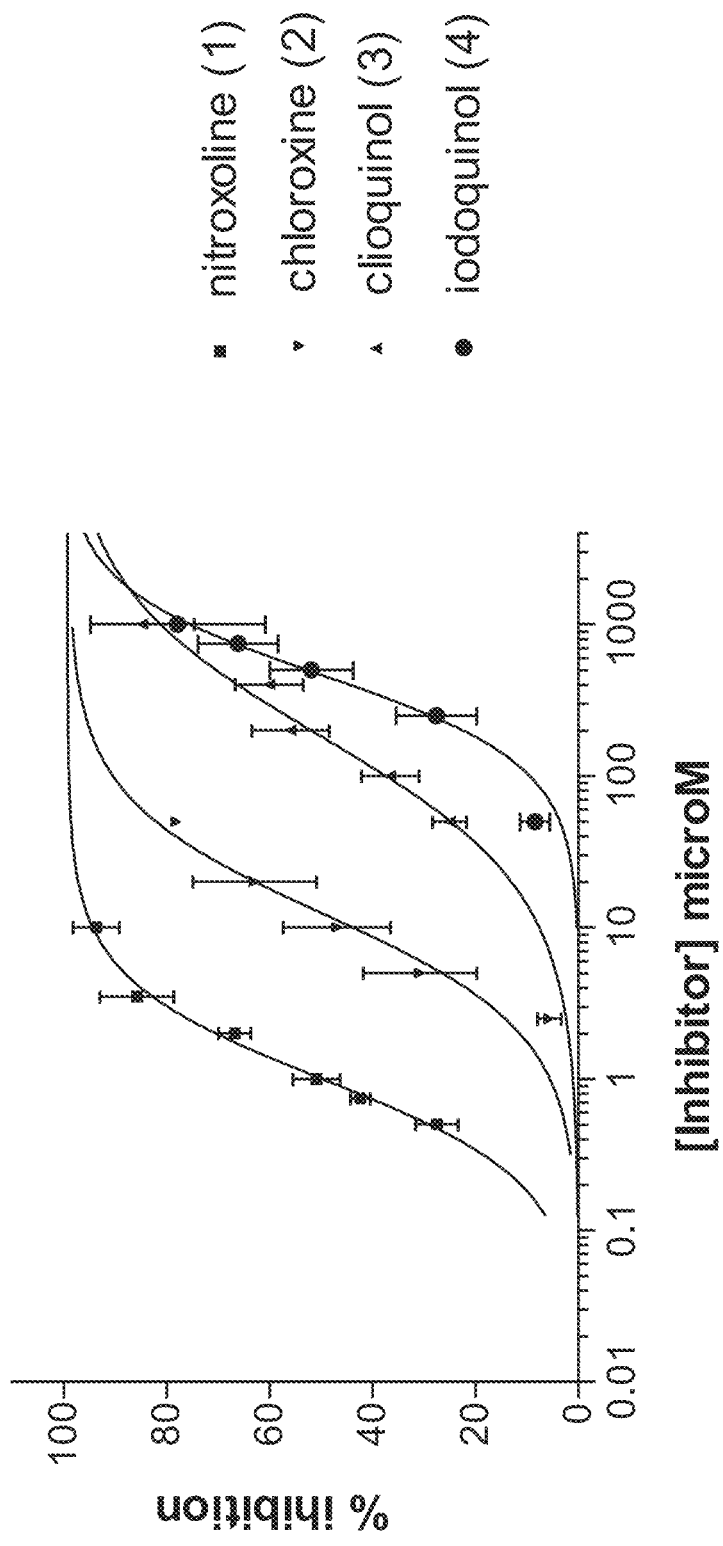
FIG. 3 (b). Hydroxyquinolines as potent inhibitors of tyrosinase

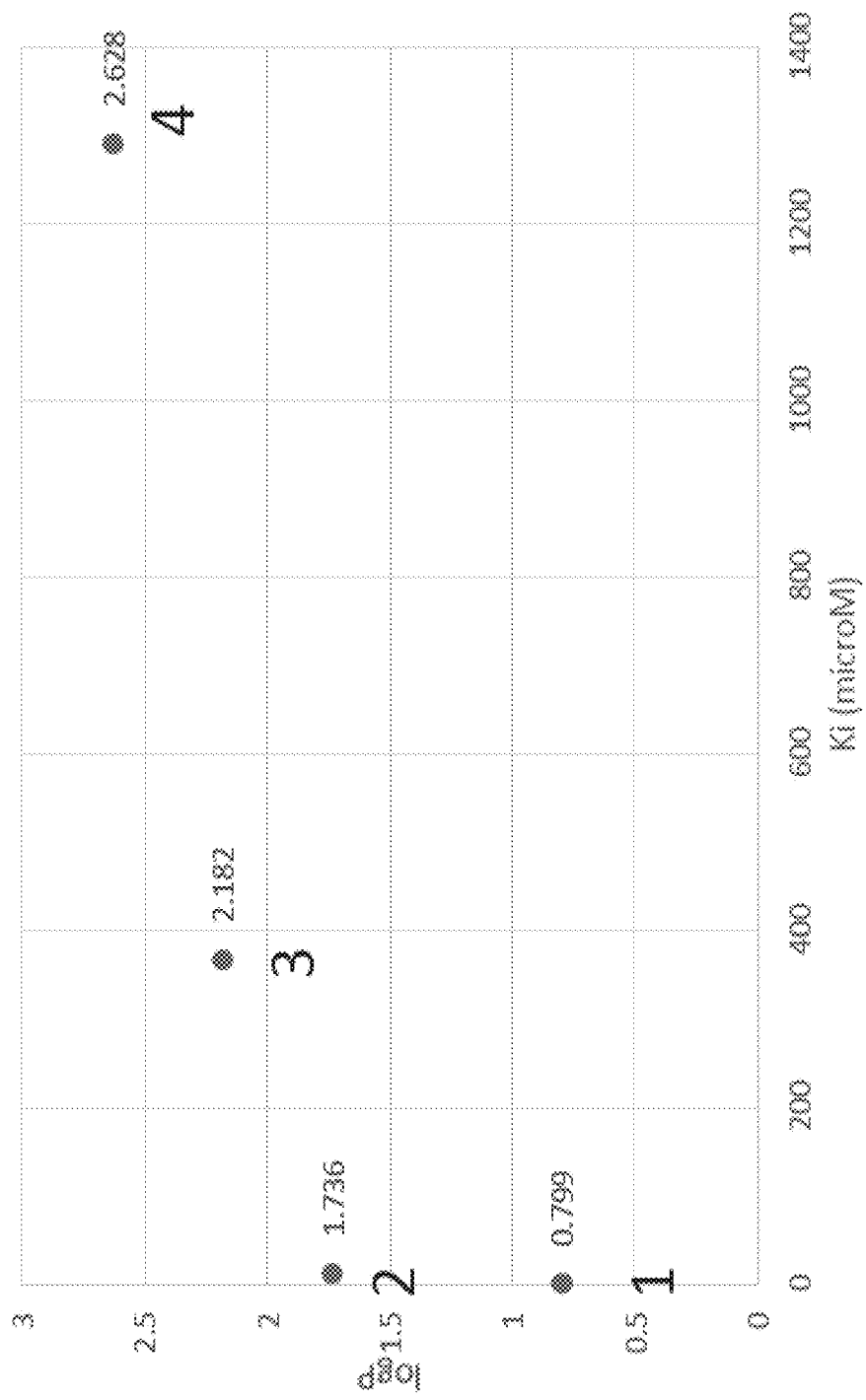
FIG. 3 (c). Plot of logP value for hydroxyquinoline drugs based on inhibitory constant values (Ki)

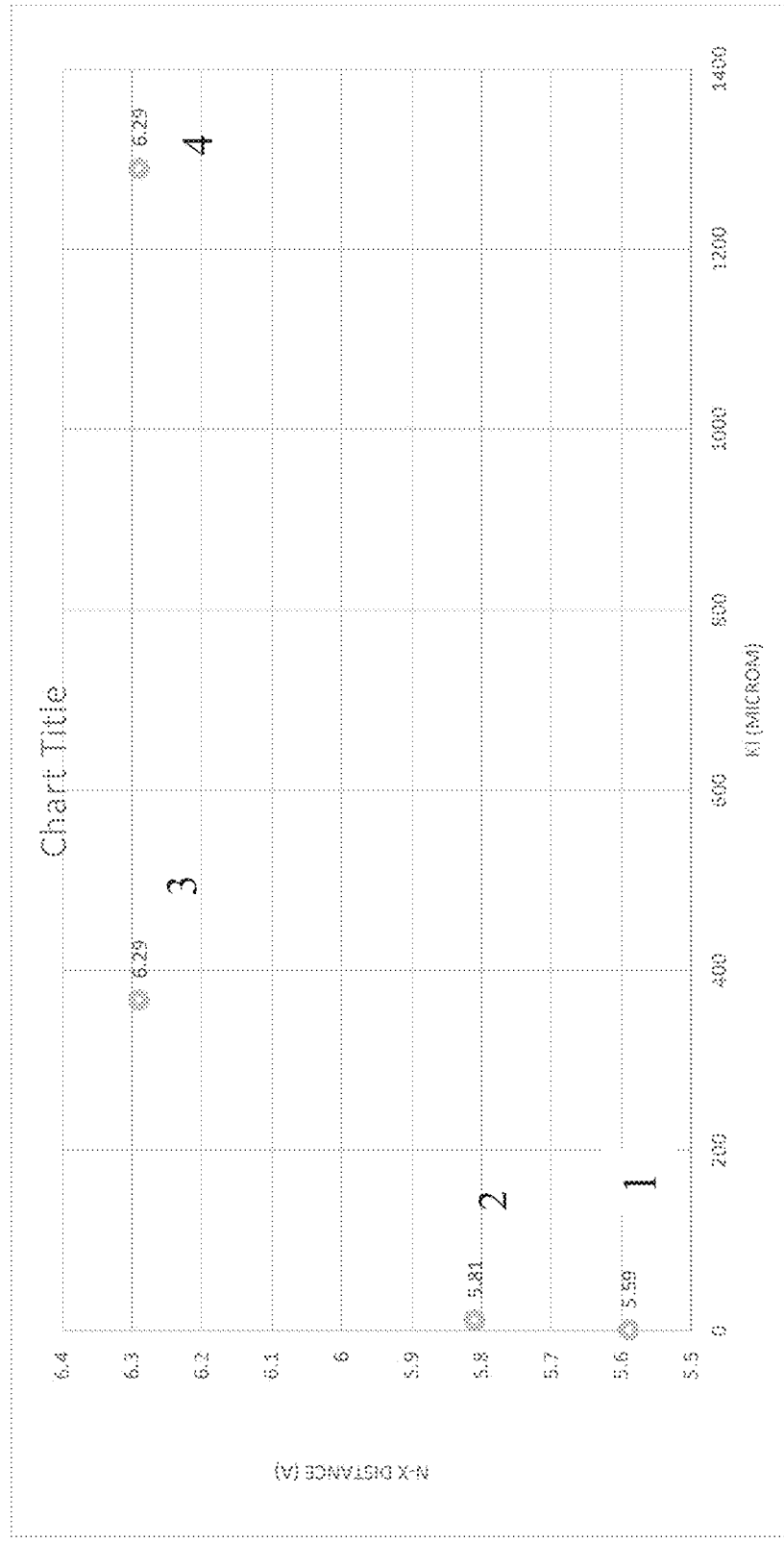
FIG. 3 (d). Plot of bond distance from nitrogen (N) to 7-position substituent (X) for hydroxyquinoline drugs based on inhibitory constant values (Ki)

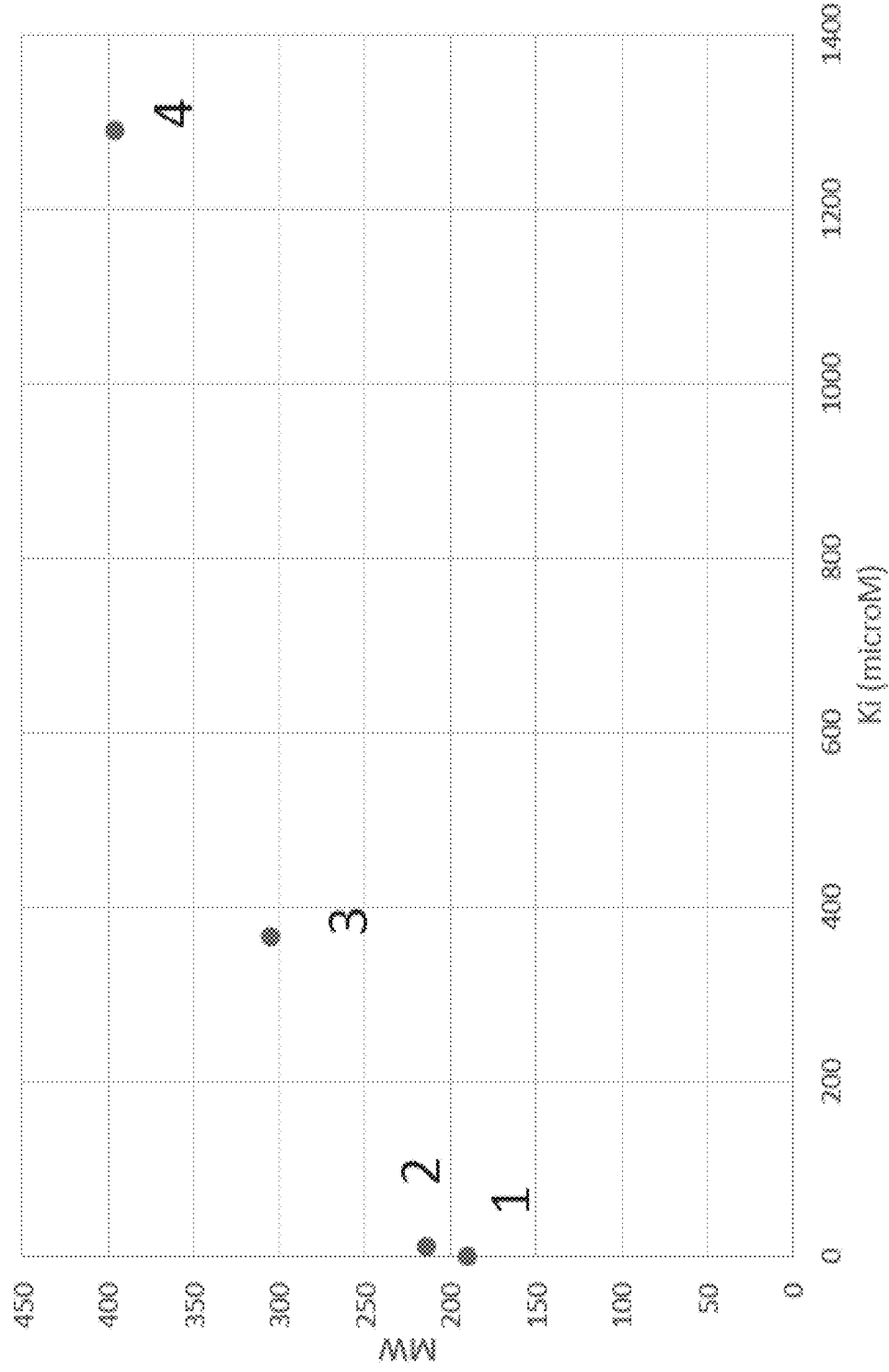
FIG. 3 (e). Plot of molecular weight of hydroxyquinoline drugs based on inhibitory constant (Ki)

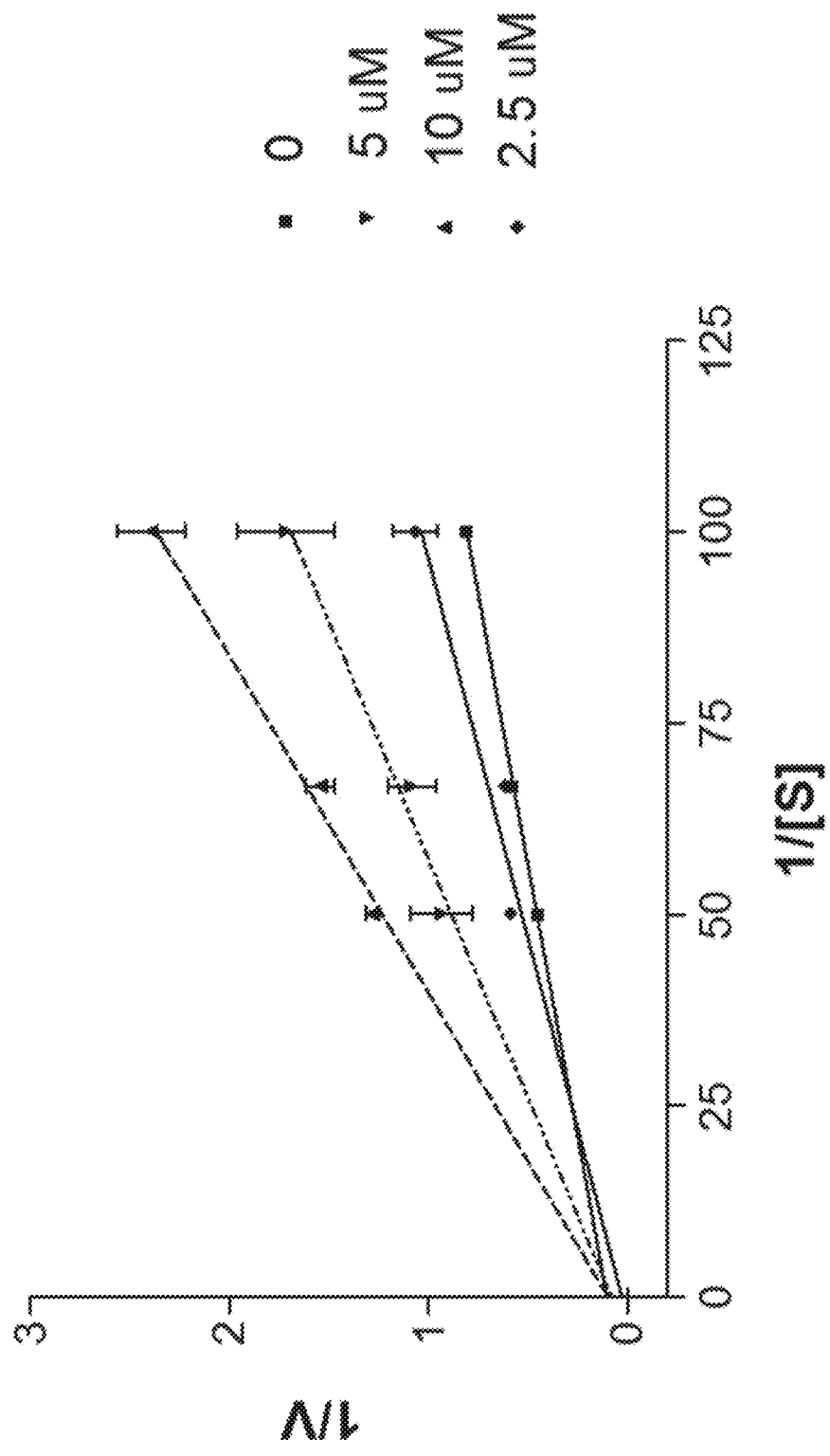
FIG. 4 (a). Kinetics of inhibition of tyrosinase by nitroxoline

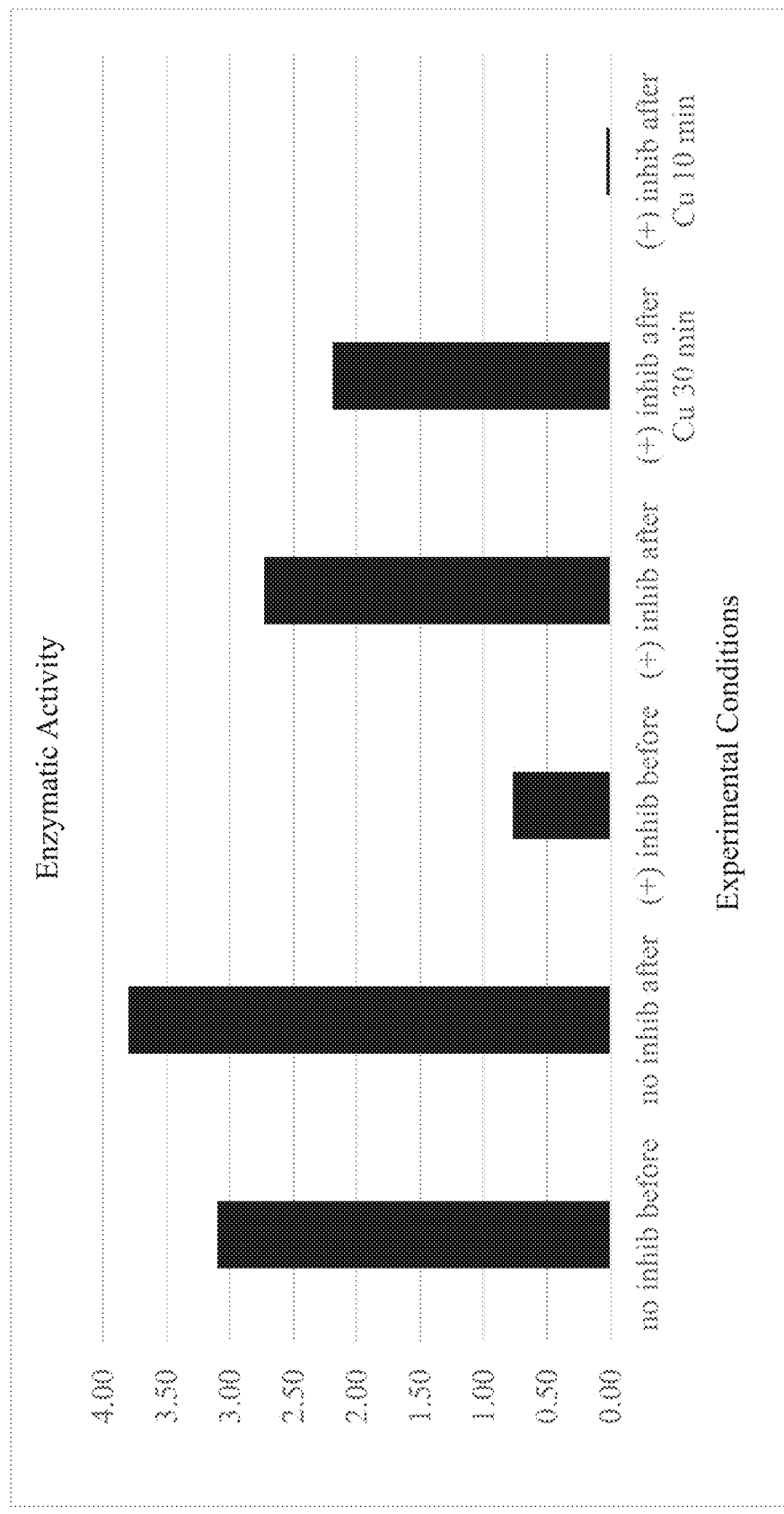
FIG. 4 (b). Enzymatic activity after ultrafiltration of nitroxoline

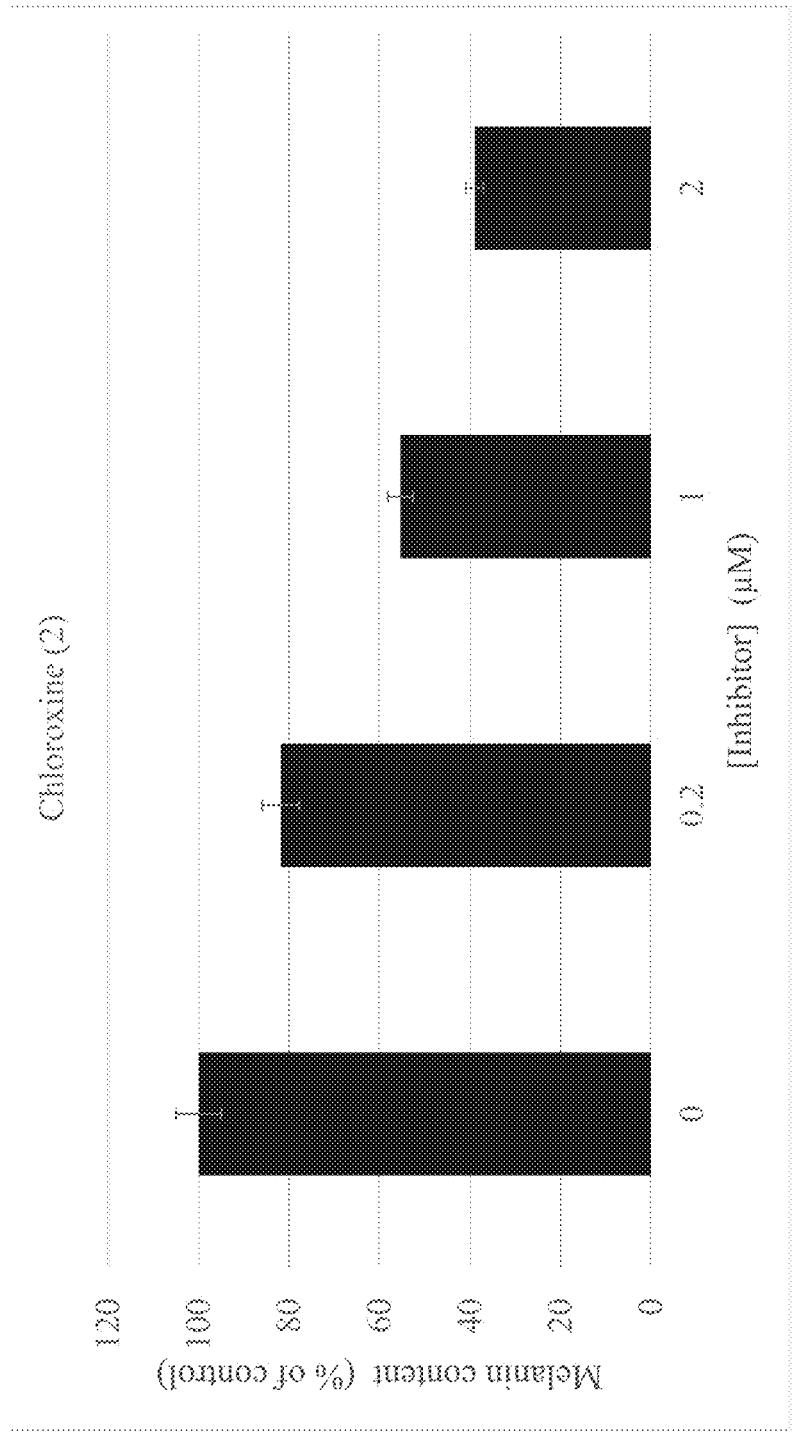
FIG. 5. Inhibition of melanin production in MNT-1 cells by chloroxine

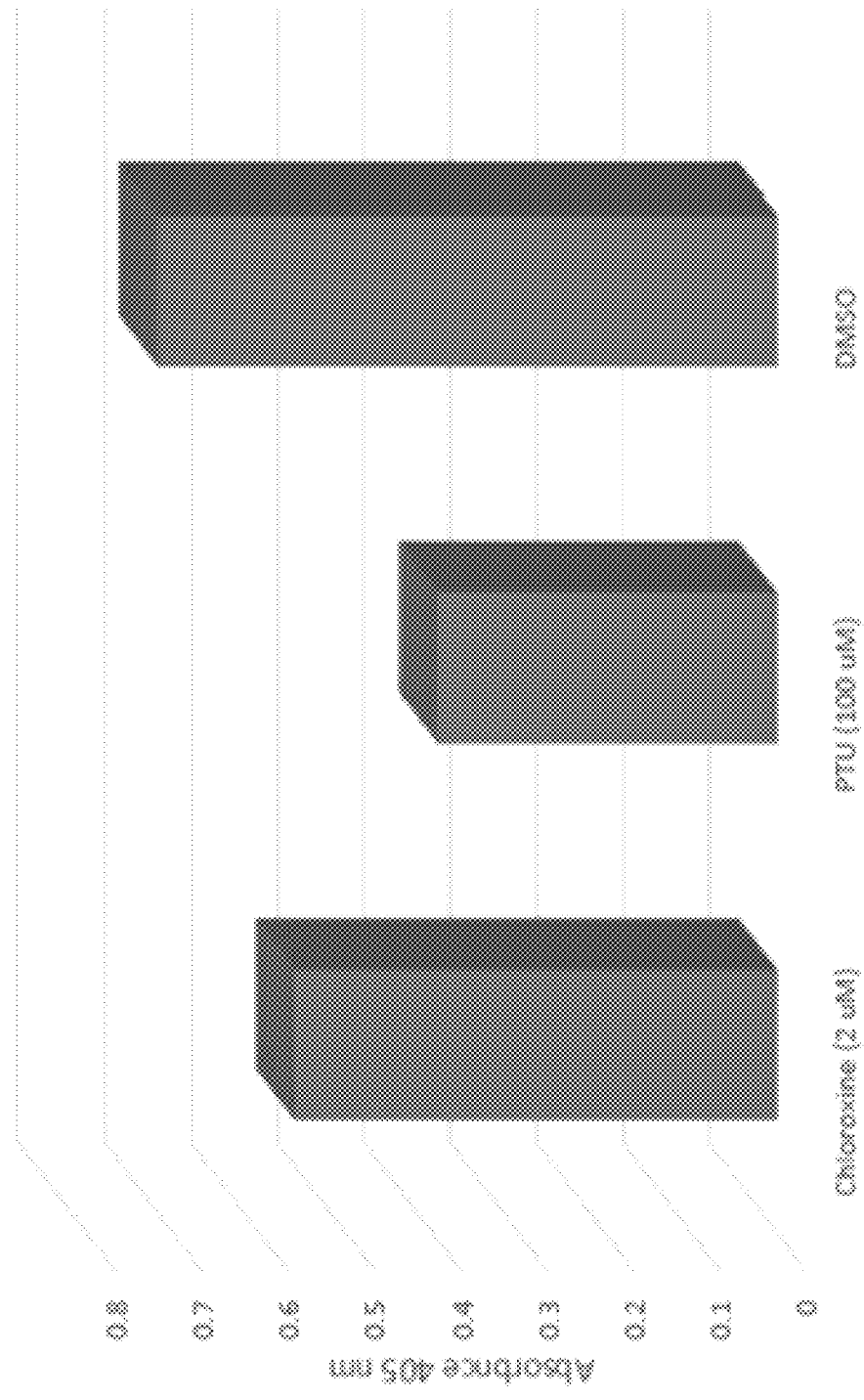
FIG. 6. Quantification of melanin in treated MNT-1 cells.

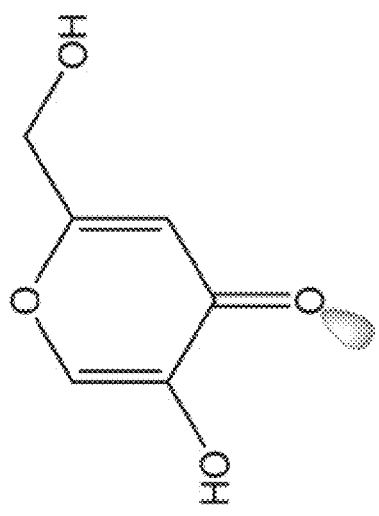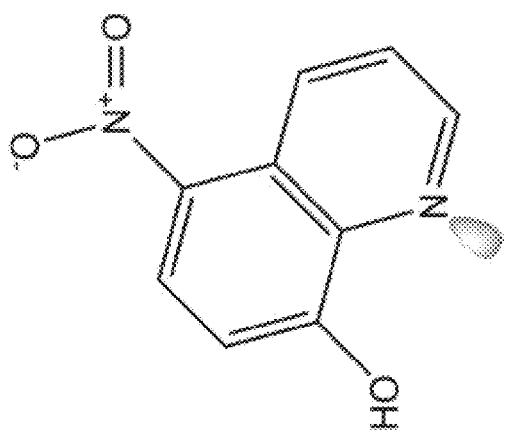
FIG. 7 (a). shows the positions of metal-binding lone pairs of electrons in the structures of (i) kojic acid (i.e., on an oxygen atom), and (ii) nitroxoline, the simplest 8-hydroxyquinoline drug (i.e., on a nitrogen atom in the ring).
(i)  Kojic acid
(ii)  Nitroxoline

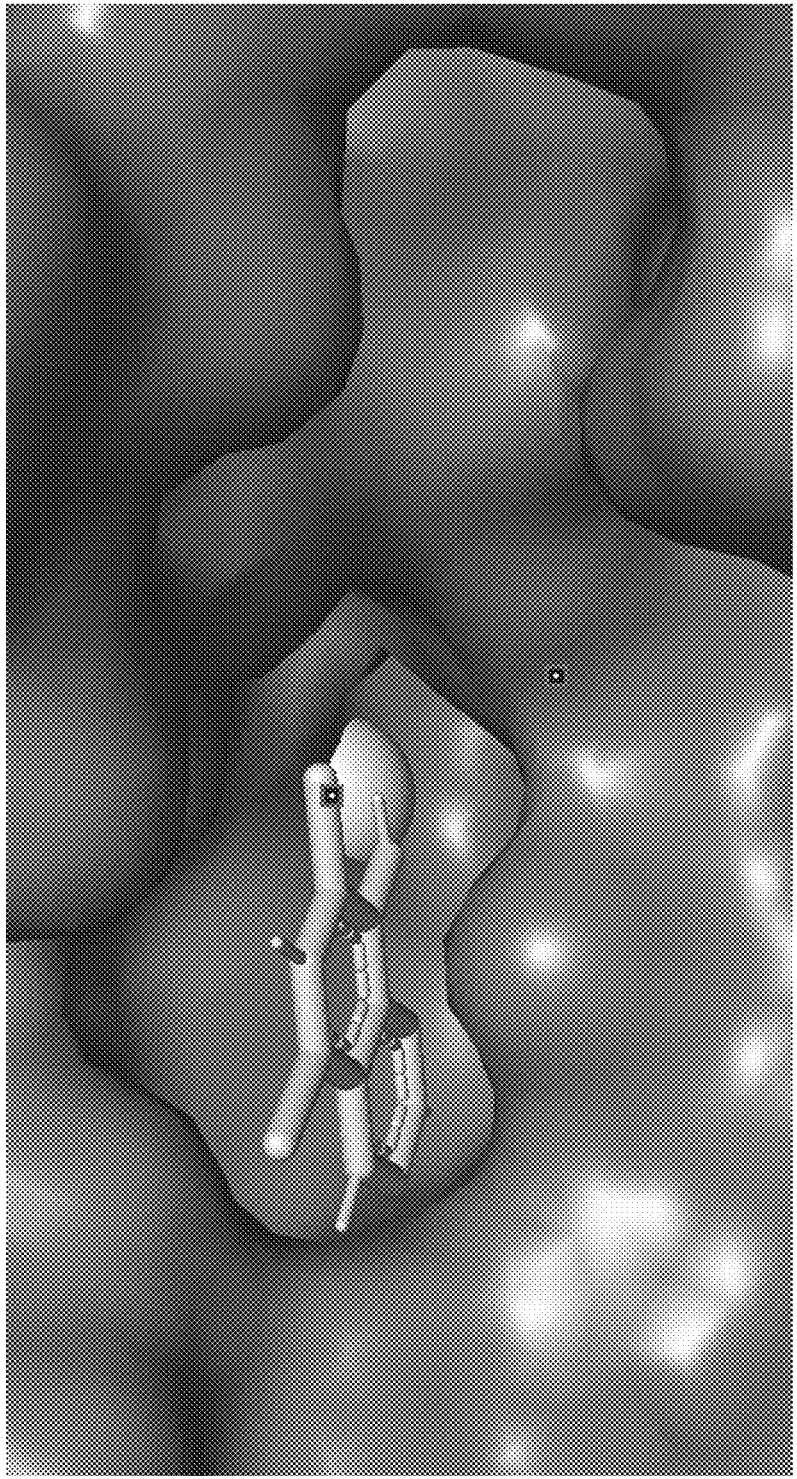
FIG. 7 (b). is an illustration representing chloroxine positioned within the active site of *A bisporus* tyrosinase when overlayed with the analogous atoms of tropolone in the tyrosinase-tropolone co-crystal structure.

HYDROXYQUINOLINE COMPOUNDS AND METHODS OF USE AS PIGMENT MODIFYING AGENTS

CROSS-REFERENCE TO PRIORITY RELATED PATENT APPLICATION

This application claims the benefit to U.S. provisional application No. 63/158,517, filed Mar. 9, 2021, which is incorporated herein by reference in its entirety.

FIELD OF THE DISCLOSURE

Pharmaceutical formulations (i.e., compositions) comprising inhibitors of the enzyme tyrosinase as depigmenting agents, and the use of such inhibitors in treating dermatologic disorders of hyperpigmentation, such as melasma and lentigo, are provided.

BACKGROUND

Pigmentation of human skin results from melanin synthesis by melanocyte cells. Melanosome organelles in the melanocytes transfer the pigment melanin into the upper keratinocyte layers and these keratinocytes are then transported to the surface of the skin by differentiation of the epidermis (see Hearing and Tsukamoto, *FASEB J.* 5:2902-2909 (1991)).

Many hyperpigmentation disorders are caused by overproduction of melanin in the skin. The pathway for melanin biosynthesis requires the enzyme tyrosinase to catalyze aerobic hydroxylation of L-tyrosine to L-dopa and subsequently to oxidize L-dopa to L-dopaquinone (FIG. 1). Mayer, A. M. et al. *Phytochemistry* 1979, 18, 193-215; Hearing, V. J. Jr., *Methods Enzym.* 1987, 142, 154-67; Solomon, E. A. et al., *Chem. Rev.* 1996, 96, 2563-605; Eicken, C. et al., *Acc. Chem. Res.* 2002, 35, 183-91; Seo, S. Y. et al., *J. Agric. Food Chem.* 2003, 51, 2837-53. The role of tyrosinase in melanin production has led researchers to develop techniques to treat hyperpigmentation by inhibiting tyrosinase. Indeed, tyrosinase inhibitors are found in current treatments for melasma, post-inflammatory hyperpigmentation, solar lentigo, and Addison's disease. For example, see Boissy, R. E. et al., *Exp. Dermatol.* 2005, 14, 601-08; Khan, K. M. et al., *Bioorg. Med. Chem.* 2006, 14, 6027-33 & 6085-88.

Conventional tyrosinase inhibitors suffer from toxicity or a lack of efficacy, however. Many currently prescribed medications include hydroquinone as a tyrosinase inhibitor. Hydroquinone is a substrate analogue of tyrosine and, like tyrosine, can undergo oxidation. Garcia-Molina M, et al., *Bioorg. Med. Chem.* 2014, 22, 3360-3369. The product of hydroquinone oxidation, benzoquinone, is a known mutagen and can damage DNA. In fact, the MSDS for benzoquinone lists it as a mutagen (human bone marrow, lymphocytes, murine embryos and lymphocytes) and a possible carcinogen; intravenous $LD_{50}$ (rat)=25 mg/Kg. Smith, M T, et al., *Environ. Health Perspect.* 1989, 82:23-29. It is cytotoxic to hepatocytes and melanocytes and may be carcinogenic. Rossi, L. et al., *Arch. Biochem. Biophys.* 1986, 251:25-35. For these reasons, the use of hydroquinone in cosmetic products has been banned in the EU. DeCaprio, A. P., Crit. Rev. Toxicol. 1999, 29:283-330; Kasraee, B. et al. In the United States, its use has recently been severely restricted. Westerhof, W., Kooyers, T. J., *J Cosmetic Derm* 2005, 4:55-59; Schlessinger, J, *Practical Derm* 2020, 17:9.

Rhododendrol [4-(4-hydroxyphenyl)-2-butanol] (FIG. 2(a)] was used as a topical skin-lightening agent until reports surfaced that it caused leukoderma, or permanent skin whitening. Sasaki, M., et al., *Pigment Cell Melanoma Res* 2014, 27:754-763. As a result, products containing rhododendrol were recalled for use in Japan and ten other Asian countries due to cytotoxicity to melanocytes. Ito et al., *Pigment Cell Melanoma Res* 2014, 27:744-753.

The tyrosinase inhibitor kojic acid has been used in the treatment of pigmentation disorders. Similar to rhododendrol and hydroquinone, however, concerns regarding efficacy and toxicity persist. A secondary metabolite isolated from *Aspergillus albus*, kojic acid displays only high micromolar inhibition of tyrosinase Saruno, R et al., *Agric. Biol. Chem.* 1979, 43:1337-38. Additionally, concerns regarding carcinogenicity spurred Japanese officials to ban its use in skin treatments. Fuyuno, I., *Nature* 2004, 432:938.

Due to the health and efficacy concerns related to rhododendrol, kojic acid and hydroquinone-derived inhibitors, it is necessary to develop alternative treatments for hyperpigmentation.

Demand exists for new efficacious drugs that hinder overproduction of melanin in the skin. Like hydroquinone, most pigmenting agents inhibit the enzyme tyrosinase. This enzyme is a copper-containing oxidase, found within pigment-producing melanocytes of the skin, that converts the amino acid tyrosine into the intermediate dopaquinone, that eventually becomes melanin through enzyme-catalyzed and spontaneous polymerization (Sanchez-Ferrer, A. et al., *Biochim Biophys Acta* 1995, 1247(1):1-11) (FIG. 2). Multiple chemical structures have been reported as tyrosinase inhibitors in vitro, with several displaying activity on human skin (Chang, T S. *Int. J Mol. Sci* 2009, 19(6):2440-75). Many of these compounds are phenol derivatives, containing one or two hydroxyl groups on a phenyl ring (Ito, S. et al., *Pigment Cell Melanoma Res* 2014, 27(6):1149-53; Ito, S, and IFPCS, 2003, 16(3):230-36). Mechanistically they act mostly as competitive inhibitors vying for the active site with tyrosine (Pillaiyar, T. et al., *J Enzyme Inhib Med Chem* 2017, 32(1):403-25; Pillaiyar, T. et al., *J Med Chem* 2018, 61(17):7395-418). A unique feature of tyrosinase is the presence of two copper ions in the active site, that bind an oxygen molecule in a presumed "bridging dioxo" configuration prior to chemical transformation of tyrosine (Ramsden, C A and Riley, P A, *Bioorg Med Chem* 2014, 22(8):2388-95). No tyrosinase inhibitor has yet been described that interferes with its catalytic transformation through extraction of copper ions from the active site. Herein we characterize the potent depigmenting activity of hydroxyquinolines (FIG. 2), a class of approved antibiotics (Odingo, J O, et al. *Drug Dev Res* 2019, 80(5):566-72; Prachayasittikul, V., et al., *Drug Des Devel Ther* 2013, 7:1157-78). While never previously tested against tyrosinase, hydroxyquinolines have surprisingly been found to be effective inhibitors that act through a unique mechanism of action: metal chelation and extraction. This very specific mechanism and potent activity indicates that hydroxyquinolines are safe and effective depigmenting drugs.

SUMMARY

Pharmaceutical formulations (i.e., compositions) comprising tyrosinase inhibitors are provided, together with methods for treating hyperpigmentation of the skin using such formulations.

In one embodiment, pharmaceutical formulations are provided, comprising an effective amount of a tyrosinase inhibitor of formula I, shown in FIG. 3 (a), in a pharmaceutically acceptable carrier for cutaneous application, wherein X, Y, and Z are independently selected from the group consisting of H, $NO_2$, F, Cl, Br, I, CN, SO, $SO_2$, $CO_2R$, $CONR^1R^2$, lower alkyl, and $CF_3$, wherein R, $R^1$ and $R^2$ independently are selected from the group consisting of H and lower alkyl, provided that at least one of X or Y is $NO_2$, F, Cl, Br, I, CN, SO, SO2, $CO_2R$, $CONR^1R^2$, or $CF_3$.

In some embodiments, methods are provided for treating a hyperpigmentary disorder involving administering to a patient suffering from the hyperpigmentary disorder an effective amount of a dermatologically acceptable pharmaceutical composition containing an effective amount of a tyrosinase inhibitor of formula I as described above, where the composition optionally contains an effective amount of a second dermatologically active compound. The second dermatologically active compound may be, for example, a sunscreen or an exfoliant. In certain embodiments, X may be $NO_2$, CN, $SO_2R$ or $CF_3$ and Y and/or Z may be H. In specific embodiment, Z is H. In further embodiments, X is Cl and Y is Cl, Br, or I, and Z is H or Me. In a particular embodiment, X is Cl and Y is Cl or I. In a further embodiment, X and Y are Br and Z is H. In yet a further embodiment X and Y are I and Z is H and in a still further embodiment Me, Y is Br and Z is H. In the disclosed methods the hyperpigmentary disorder may be, for example, melasma, chloasma, lentigines, senile lentigo, an irregular hyperpigmentation related to photoaging, freckles, a post-inflammatory hyperpigmentation due to an abrasion, a burn, a scar, dermatosis, a contact allergy or naevi.

In yet another embodiment, an effective amount of a tyrosinase inhibitor of formula (I) in a pharmaceutically acceptable carrier for cutaneous application is combined with any one or more of a sunscreen, exfoliant, retinoid, absorption enhancer, anti-inflammatory agent, antioxidant, or steroid and used to treat hyperpigmentary disorders.

BRIEF DESCRIPTION OF THE DRAWINGS

FIG. 1 depicts the chemical transformation of tyrosine to L-dopa, and then to dopaquinone, both catalyzed by tyrosinase.

FIG. 2 (a)-(d) show the structures of several inhibitors: (a) rhododendrol, (b) kojic acid, (c) chloroxine, and (d) nitroxoline.

FIG. 3 (a) shows the formula I structure, as well as a table of certain approved hydroxyquinoline drugs against tyrosinase, and their inhibition constant (Ki) values.

FIG. 3 (b) shows a graph of the inhibition of tyrosinase activity by a variety of hydroxyquinoline drugs. In vitro fluorescence assays using mushroom tyrosinase were performed in 50 mM sodium phosphate buffer, pH 7.4 with PAP-AMC as substrate. Varying concentrations of inhibitors were used as indicated. Data represent the mean±SD of three independent experiments. Nitroxoline (1) and chloroxine (2) show the lowest $IC_{50}$ values.

FIG. 3 (c) shows a plot of the log P value for each the identified hydroxyquinoline drugs based on its Ki value.

FIG. 3 (d) shows a plot of the distance between the nitrogen atom (N) and the 7-position substituent (X) for each of the identified hydroxyquinoline drugs based on its Ki value.

FIG. 3 (e) shows a plot of the molecular weight of each of the identified hydroxyquinoline drugs based on its Ki value.

FIG. 4 (a) depicts a plot showing the kinetics of inhibition of tyrosinase by nitroxoline at the μM concentrations noted.

The experiment was performed in triplicate at pH 7.4 and data were plotted according to Lineweaver-Burk. Data represent the mean±SD of three independent experiments.

FIG. 4 (b) shows the effect of nitroxoline on enzymatic activity after ultrafiltration. Bars represent percentage of initial activity (a) without inhibitor, (b) with 5 μM inhibitor before ultrafiltration, (c) with 5 μM inhibitor after ultrafiltration and 30-minute incubation with 0.1 mM final concentration copper sulfate, (d) 10-minute incubation with 0.1 mM final concentration copper sulfate, and (e) after ultrafiltration and no exogenous copper sulfate.

FIG. 5 shows the effect of chloroxine to inhibit melanin production in MNT-1 cells. Cells were incubated with chloroxine for 3 days, and then harvested, with melanin quantified after cell lysis, measuring absorbance at 405 nm.

FIG. 6 depicts the reduction in melanin biosynthesis in MNT-1 cells by chloroxine, relative to the positive control phenylthiourea (PTU), a tyrosinase inhibitor commonly used as a melanin synthesis blocker.

FIG. 7 (a) is a diagram showing the positions of metal-binding lone pairs of electrons in the structures of (i) nitroxoline, the simplest 8-hydroxyquinoline drug; and (ii) kojic acid.

FIG. 7 (b) is an illustration representing chloroxine positioned within the active site of *A bisporus* tyrosinase when overlayed with the analogous atoms of tropolone in the tyrosinase-tropolone co-crystal structure.

DETAILED DESCRIPTION

Compositions and methods are provided for treating hyperpigmentation disorders of the skin. The compositions contain tyrosinase inhibitors and, optionally, additional compounds having dermatological activity. These additional compounds can exhibit, for example, exfoliating activity or act as sunscreens. The compositions may be used for treating disorders such as melasma, chloasma, lentigines, senile lentigo, an irregular hyperpigmentation related to photoaging, freckles, a post-inflammatory hyperpigmentation due to an abrasion, a burn, a scar, dermatosis, a contact allergy and naevi. The compositions described herein inhibit melanogenesis but are either non-toxic to melanocytes or have lower toxicity that existing compositions. Current agents that are used to treat the spectrum of skin hyperpigmentation conditions are hampered by cellular toxicity and efficacy issues, motivating discovery of safer and more effective depigmenting agents (Draelos, Z D. *Dermatol Ther* 2007, 20(5):308-13; Westerhof, W. and Kooyers, T J. *J Cosmet Dermatol*, 2005, 4(2):55-59).

Hyperpigmentation disorders, such as melasma and post-inflammatory hyperpigmentation, are of particular concern, since there are few safe and effective treatments (Chandra, M., et al., *Venereol*, 2012, 92(3):232-35) (Chaowattanapanit, S. et al., *J Am Acad Dermatol* 2017, 77(4):607-21). The small molecule, hydroquinone, currently the only approved drug to treat hyperpigmentation in the United States, faces regulatory scrutiny due to its possible carcinogenicity, and its use in both the United States and elsewhere has recently been severely restricted (Westerhof and Kooyers, 2005; Liu, Y., et al., *J Am Acad Dermatol* 2021, 85(6):1608-10). The clinical efficacy of select hydroxyquinolines to treat disorders of hyperpigmentation is being actively investigated.

Discovering new applications of existing drugs toward diseases for which they were not originally developed is termed "repurposing" or "repositioning." As the cost of bringing a new drug to market continues to increase, repurposing a drug already proven safe through clinical trials and post-market monitoring becomes very attractive (Pushpakom, S., et al., *Nat Rev Drug Discov* 2019, 18(1):41-58). As such, repurposing established drugs represents an expedient route to an effective therapy that may stabilize an epidemic until a more targeted drug is discovered (Wang, M., et al., *Cell Res* 2020, 30(3):269-71), or for treatment of a rare disease (Cho, H G, et al., *J Invest Dermatol* 2016, 136(7): 1517-20; Lee, et al., 2022). Disorders of pigmentation are a group of conditions that arise from undesired under- or overproduction of the pigment melanin in the skin (Nordlund, J J, et al., *J Am Acad Dermatol* 1985, 12(2 Pt 1):359-63). These diseases, including vitiligo and melasma, represent a significant medical burden on individuals, particularly on patients of color (Ebanks, J P, et al., *Int J Mol Sci* 2009, 10(9):4066-87; Maymone, M B C, et al., *J Am Acad Dermatol* 2017, 77(4):775-78).

FIG. 1 depicts the chemical transformation of tyrosine to L-dopa, and then to dopaquinone, both catalyzed by tyrosinase. Because it catalyzes the rate-limiting step in the production of the skin pigment melanin, the enzyme tyrosinase is a target to identify inhibitors as candidates to treat hyperpigmentation. We have previously demonstrated that, using a novel fluorescent tyrosinase substrate, very potent melanin production blockers could be discovered through high throughput screening of a small molecule library (Germanas, J, et al., *Bioorg Med Chem Lett* 2007, 17(24):2638-44).

The terms and words used in this detailed description and claims are not limited to conventional definitions but, rather, are used to enable a clear and consistent understanding of the disclosure. Accordingly, it should be apparent to those skilled in the art that the following description of various embodiments is provided for illustration purpose only and not for the purpose of limiting the disclosure with respect to the appended claims and their equivalents.

Structures of Hydroxyquinolines

The tyrosinase inhibitors compounds have the general 8-hydroxyquinoline structure of Formula I (FIG. 2 (*a*)-(*c*), (*e*); FIG. 3 (*a*)). In this structure at least one of X and Y is an electron-withdrawing group. Without being bound by theory, it is believed that presence of an electron withdrawing group at the 5- or 7-position of the 8-hydroxyquinoline nucleus leads to improved tyrosinase inhibition by increasing the acidity of the 8-hydroxy moiety. The electron withdrawing group can be, for example, a halide, trihalomethyl, nitro, nitrile, ester, amide, sulfoxide, sulfone, or sulfonyl moiety. Provided that at least one electron-withdrawing moiety is present at either the 5- (X) or 7- (Y) position, the other substituents, including the Z moiety at the 1-position, may be independently selected from the group consisting of H, $NO_2$, F, Cl, Br, I, CN, S(O)R, $SO_2R$, $SO_3H$, $CO_2R$, $CONR^1R^2$, lower alkyl, and $CF_3$. R, $R^1$ and $R^2$ independently are H or lower alkyl. Advantageously, Z is either H or lower alkyl, including substituted alkyl.

The four hydroxyquinoline drugs identified in FIG. 3 were selected for study, showing the general structure (formula I): nitroxoline (1), chloroxine (2), clioquinol (3), and iodoquinol (4), as well as their formulas and inhibitory constants (Ki). The drugs had previously been approved by the US Food and Drug Administration as antimicrobial agents. None, however, had ever been studied as a pigmentation inhibitor. Molecules in this class contain a heterocyclic aromatic quinoline core substituted at the 8-position with a hydroxyl group. Further substitutions, primarily at the 5- and 7-position, diversify the compounds (FIG. 3 (*a*) Table). These molecules were chosen for their diverse array of substituents with varying steric, electronic, molecular weight, and solubility characteristics. None of the compounds displayed a fluorescence signal in the tyrosinase assay at the wavelengths used that would interfere with the activity assay.

Inhibition of Tyrosinase by Hydroxyquinolines

Initial screening of the hydroxyquinoline drugs for inhibitory activity was performed with mushroom tyrosinase (Espin, J C, et al., *J Biochem* 2000, 267(5):1270-79). The use of tyrosinase from this source is justified by its ready availability and substrate specificity to the mammalian enzyme (Hearing, V J, et al., *Biochim Biophys Acta* 1980, 611(2):251-68). Additionally, inhibitors found to have strong affinity for the mammalian enzyme possessed very close structural similarity to those that potently blocked the mushroom tyrosinase enzyme (Hornyak, T J. *J Invest Dermatol* 2018, 138(7):1470-72).

The previously described fluorescence-based, tyrosinase assay using the substrate PAP-AMC was used to assess inhibition of enzyme activity by the hydroxyquinoline drugs (Germanas et al., 2007). This assay possesses unique advantages due to its sensitivity and its unique ability to specifically measure the rate of the first step of the reaction, the so-called monophenolase conversion of tyrosine into L-DOPA (FIG. 1) (Germanas, J, et al., 2007). Whereas the commonly used MBTH colorimetric assay is a more popular method of assessing compounds for inhibition of tyrosinase, this assay in fact measures the diphenolase (L-DOPA oxidase) activity of the enzyme (Winder, A J and Harris, H, *Eur J Biochem* 1991, 198(2):317-26). This is the faster of the two steps of the transformation of tyrosine into dopaquinone and, using it to identify inhibitors may not correlate to their blockage of melanin production in vivo.

The antibiotic, nitroxoline (1), is a potent inhibitor (Ki=0.9 μM) of tyrosinase. This strong and specific interaction with tyrosinase makes nitroxoline and related compounds as described herein clinically useful as skin whitening agents. Three additional drugs in the hydroxyquinoline class (chloroxine (2), clioquinol (3) and iodoquinol (4)) also inhibit tyrosinase. Chloroxine displayed inhibitory activity against mushroom tyrosinase with a Ki of approximately 12 μM, while clioquinol and iodoquinol displayed much higher Ki levels, 367 and 1290 μM, respectively.

Examples of compounds of formula I are shown in the Table in FIG. 3 (*a*). Each of the compounds has achieved regulatory approval for use as an antibacterial, antifungal or antiprotozoal. All four compounds exhibited a dose-dependent inhibition of the monophenolase activity of tyrosinase, but to starkly varying degrees (FIG. 3(*b*)). The 5-nitro-substituted derivative nitroxoline (1) was the most potent inhibitor, with a Ki value 0.9 μmol/L. On the other hand, iodoquinol (4) was the least active with a high micromolar inhibitory constant. At higher concentrations, the heavier molecular weight compounds clioquinol (3) and iodoquinol (4) were less soluble in aqueous solution. The smaller compounds, nitroxoline (1) and chloroxine (2), did not show evidence of insolubility under the assay conditions.

Further investigation showed that the hydroxyquinolines reversibly extract copper from the enzyme. Hydroxyquinolines are particularly well known as strong ligands for transition metals, particularly copper (II) (Gershon, H, *J Med Chem* 1974, 17(8):824-27). Without being bound by theory, it appears that a reasonable model for the mechanism of hydroxyquinoline action involves binding to the active site, coordination of a copper ion, followed by extraction.

Type of Enzyme Inhibition by Hydroxyquinolines

The specific type of enzyme inhibition of tyrosinase by hydroxyquinolines was investigated via kinetics assays with the drug nitroxoline (1). Initial velocities of the reaction of PAPAMC in the fluorescence assay were measured with varying concentrations of substrate and of nitroxoline and were subsequently plotted to create a series of Lineweaver-Burk plots. Intersection of the individual plots on the y-axis of the plot demonstrate that nitroxoline behaves as a competitive inhibitor (FIG. 4(a)). A reasonable conclusion, based on their structural similarity, is that the rest of the hydroxyquinoline drugs would also inhibit tyrosinase in a competitive manner.

To gain further insight into the mode of action of the hydroxyquinoline drugs, residual enzyme activity was assessed after separation of the drug from the enzyme. This is generally done to assess whether the inhibitor acts in a reversible or irreversible manner. After incubation and measurement of tyrosinase activity, the drug nitroxoline (1) was separated from the reaction mixture in a Centricon centrifugal filter device, and enzymatic activity remeasured with fresh PAPAMC substrate.

When residual activity was measured after ultracentrifugation, less than 10% of the original activity remained (FIG. 4(b)). However, if the resulting enzyme concentrate was incubated with exogenous copper sulfate and then assayed with PAPAMC, substantial recovery of original enzyme activity was observed. This reconstitution of tyrosinase activity appears to be dependent on the amount of time the enzyme solution is exposed to copper: a much smaller fraction of activity is recovered when the enzyme is incubated with copper for 10 minutes, rather than 30 minutes. These observations suggest, that nitroxoline extracts copper from the enzyme active site through formation of a drug-copper complex.

To gain greater insight into the structure-activity relationships of hydroxyquinolines with tyrosinase, molecular modeling studies were performed. A potential explanation for the surprising avidity of hydroxyquinolines to tyrosinase was developed by superimposing the metal-binding lone electron pairs of 8-hydroxyquinoline (nitrogen and hydroxyl) with those of kojic acid (Lachowicz, J I, et al., *J Inorg Biochem* 2015, 151:36-43; Nurchi, V M, et al., *J Inorg Biochem* 2018, 189:103-14). Overlay of the two structures reveals exact alignment and orientation of the hydroxyl and the heteroatom lone pairs (FIG. 7 (a)).

The structure of chloroxine (2) was also superimposed onto that of 2-hydroxytropolone (Espin, J C and Wichers, H J. *J Agric Food Chem* 1999, 47(7):2638-44) (a molecule that has the same functional group orientations as kojic acid) in the crystal structure of the mushroom tyrosinase-inhibitor complex (Ismaya, W T, et al., *Biochem* 2011, 50(24):5477-86). A close fit without adverse steric interactions resulted (FIG. 7 (b)). The chlorine atoms of chloroxine faced outward, while the nitrogen and hydroxy groups oriented toward the copper atoms. Without being bound by theory, this fit provides a possible explanation as to why hydroxyquinolines with larger 5-position substituents, such as iodoquinol (4), were less active inhibitors; this was due to adverse steric interactions with the active site periphery. This was further supported by quantitative structure-activity relationship analysis: inhibitory activity did not correlate with either compound partition coefficient log P, or C5-X bond length, but did correlate with molecular size (FIG. 3 (c)-(e)).

Substituted Groups

In general, "substituted" refers to an organic group as defined below (e.g., an alkyl group) in which one or more bonds to a hydrogen atom contained therein are replaced by a bond to non-hydrogen or non-carbon atoms. Substituted groups also include groups in which one or more bonds to a carbon(s) or hydrogen(s) atom are replaced by one or more bonds, including double or triple bonds, to a heteroatom. Thus, a substituted group will be substituted with one or more substituents, unless otherwise specified. In some embodiments, a substituted group is substituted with 1, 2, 3, 4, 5, or 6 substituents. Examples of substituent groups include: halogens (i.e., F, Cl, Br, and I); hydroxyls; alkoxy, alkenoxy, alkynoxy, aryloxy, aralkyloxy, heterocyclyloxy, and heterocyclylalkoxy groups; carbonyls (oxo); carboxyls; esters; ethers; urethanes; oximes; hydroxylamines; alkoxyamines; aralkoxyamines; thiols; sulfides; sulfoxides; sulfones; sulfonyls; sulfonamides; amines; N-oxides; hydrazines; hydrazides; hydrazones; azides; amides; ureas; amidines; guanidines; enamines; imides; isocyanates; isothiocyanates; cyanates; thiocyanates; imines; nitro groups; nitriles (i.e., CN); and the like.

Substituted ring groups such as substituted cycloalkyl, aryl, heterocyclyl and heteroaryl groups also include rings and fused ring systems in which a bond to a hydrogen atom is replaced with a bond to a carbon atom. Therefore, substituted cycloalkyl, aryl, heterocyclyl and heteroaryl groups can also be substituted with substituted or unsubstituted alkyl, alkenyl, and alkynyl groups as defined below.

Alkyl groups include straight chain and branched alkyl groups having from 1 to about 20 carbon atoms, and typically from 1 to 12 carbons or, in some embodiments, from 1 to 8, 1 to 6, or 1 to 4 carbon atoms. Alkyl groups further include cycloalkyl groups as defined below. Examples of straight chain alkyl groups include those with from 1 to 8 carbon atoms such as methyl, ethyl, n-propyl, n-butyl, n-pentyl, n-hexyl, n-heptyl, and n-octyl groups. Examples of branched alkyl groups include, but are not limited to, isopropyl, iso-butyl, sec-butyl, tert-butyl, neopentyl, isopentyl, and 2,2-dimethylpropyl groups. Representative substituted alkyl groups can be substituted one or more times with substituents such as those listed above.

Cycloalkyl groups are cyclic alkyl groups such as, but not limited to, cyclopropyl, cyclobutyl, cyclopentyl, cyclohexyl, cycloheptyl, and cyclooctyl groups. In some embodiments, the cycloalkyl group has 3 to 8 ring members, whereas in other embodiments the number of ring carbon atoms range from 3 to 5, 3 to 6, or 3 to 7. Cycloalkyl groups further include mono-, bicyclic and polycyclic ring systems, such as, for example bridged cycloalkyl groups as described below, and fused rings, such as, but not limited to, decalinyl, and the like. In some embodiments, polycyclic cycloalkyl groups have three rings. Substituted cycloalkyl groups can be substituted one or more times with, non-hydrogen and non-carbon groups as defined above. However, substituted cycloalkyl groups also include rings that are substituted with straight or branched chain alkyl groups as defined above. Representative substituted cycloalkyl groups can be mono-substituted or substituted more than once, such as, but not limited to, 2,2-, 2,3-, 2,4- 2,5- or 2,6-disubstituted cyclohexyl groups, which can be substituted with substituents such as those listed above. Cycloalkyl groups can also be bridged cycloalkyl groups in which two or more hydrogen atoms are replaced by an alkylene bridge, wherein the bridge can contain 2 to 6 carbon atoms if two hydrogen atoms are located on the same carbon atom, or 1 to 5 carbon atoms, if the two hydrogen atoms are located on adjacent carbon atoms, or 2 to 4 carbon atoms if the two hydrogen atoms are located on carbon atoms separated by 1 or 2 carbon atoms. Bridged cycloalkyl groups can be bicyclic, such as, for example bicyclo[2.1.1]hexane, or tricyclic, such as, for example, adamantyl. Representative bridged cycloalkyl groups include bicyclo[2.1.1]hexyl, bicyclo[2.2.1]heptyl, bicyclo[3.2.1]octyl, bicyclo[2.2.2]octyl, bicyclo[3.2.2]nonyl, bicyclo[3.3.1]nonyl, bicyclo[3.3.2]decanyl, adamantyl, noradamantyl, bornyl, or norbornyl groups. Substituted bridged cycloalkyl groups can be substituted one or more times with non-hydrogen and non-carbon groups as defined above. Representative substituted bridged cycloalkyl groups can be mono-substituted or substituted more than once, such as, but not limited to, mono-, di- or tri-substituted adamantyl groups, which can be substituted with substituents such as those listed above.

Cycloalkylalkyl groups are alkyl groups as defined above in which a hydrogen or carbon bond of an alkyl group is replaced with a bond to a cycloalkyl group as defined above. In some embodiments, cycloalkylalkyl groups have from 4 to 20 carbon atoms, 4 to 16 carbon atoms, and typically 4 to 10 carbon atoms. Substituted cycloalkylalkyl groups can be substituted at the alkyl, the cycloalkyl or both the alkyl and cycloalkyl portions of the group. Representative substituted cycloalkylalkyl groups can be mono-substituted or substituted more than once, such as, but not limited to, mono-, di- or tri-substituted with substituents such as those listed above.

Alkenyl groups include straight and branched chain and cycloalkyl groups as defined above, except that at least one double bond exists between two carbon atoms. Thus, alkenyl groups have from 2 to about 20 carbon atoms, and typically from 2 to 12 carbons or, in some embodiments, from 2 to 8, 2 to 6, or 2 to 4 carbon atoms. In some embodiments, alkenyl groups include cycloalkenyl groups having from 4 to 20 carbon atoms, 5 to 20 carbon atoms, 5 to 10 carbon atoms, or even 5, 6, 7, or 8 carbon atoms. Examples include, but are not limited to vinyl, allyl, —CH=CH(CH$_3$), —CH=C(CH$_3$)$_2$, —C(CH$_3$)=CH$_2$, —C(CH$_3$)=CH(CH$_3$), CH=CHCH=CH$_2$, C(CH$_2$CH$_3$)=CH$_2$, cyclohexenyl, cyclopentenyl, cyclohexadienyl, butadienyl, pentadienyl, and hexadienyl, among others. Representative substituted alkenyl groups can be mono-substituted or substituted more than once, such as, but not limited to, mono-, di- or tri-substituted with substituents such as those listed above.

Cycloalkenylalkyl groups are alkyl groups as defined above in which a hydrogen or carbon bond of the alkyl group is replaced with a bond to a cycloalkenyl group as defined above. Substituted cycloalkylalkenyl groups can be substituted at the alkyl, the cycloalkenyl or both the alkyl and cycloalkenyl portions of the group. Representative substituted cycloalkenylalkyl groups can be substituted one or more times with substituents such as those listed above.

Alkynyl groups include straight and branched chain alkyl groups, except that at least one triple bond exists between two carbon atoms. Thus, alkynyl groups have from 2 to about 20 carbon atoms, and typically from 2 to 12 carbons or, in some embodiments, from 2 to 8, 2 to 6, or 2 to 4 carbon atoms. Examples include, but are not limited to —C≡CH, —C≡C(CH$_3$), —C≡C(CH$_2$CH$_3$), —CH$_2$C≡CH, —CH$_2$C≡C(CH$_3$), and —CH$_2$C≡C(CH$_2$CH$_3$), among others. Representative substituted alkynyl groups can be mono-substituted or substituted more than once, such as, but not limited to, mono-, di- or tri-substituted with substituents such as those listed above.

Aryl groups are cyclic aromatic hydrocarbons that do not contain heteroatoms. Aryl groups include monocyclic, bicyclic and polycyclic ring systems. Thus, aryl groups include, but are not limited to, phenyl, azulenyl, heptalenyl, biphenylenyl, indacenyl, fluorenyl, phenanthrenyl, triphenylenyl, pyrenyl, naphthacenyl, chrysenyl, biphenyl, anthracenyl, indenyl, indanyl, pentalenyl, and naphthyl groups. In some embodiments, aryl groups contain 6-14 carbons, and in others from 6 to 12 or even 6-10 carbon atoms in the ring portions of the groups. Although the phrase "aryl groups" includes groups containing fused rings, such as fused aromatic-aliphatic ring systems (e.g., indanyl, tetrahydronaphthyl, and the like), it does not include aryl groups that have other groups, such as alkyl or halo groups, bonded to one of the ring members. Rather, groups such as tolyl are referred to as substituted aryl groups. Representative substituted aryl groups can be mono-substituted or substituted more than once. For example, monosubstituted aryl groups include, but are not limited to, 2-, 3-, 4-, 5-, or 6-substituted phenyl or naphthyl groups, which can be substituted with substituents such as those listed above.

Aralkyl groups are alkyl groups as defined above in which a hydrogen or carbon bond of an alkyl group is replaced with a bond to an aryl group as defined above. In some embodiments, aralkyl groups contain 7 to 20 carbon atoms, 7 to 14 carbon atoms or 7 to 10 carbon atoms. Substituted aralkyl groups can be substituted at the alkyl, the aryl or both the alkyl and aryl portions of the group. Representative aralkyl groups include but are not limited to benzyl and phenethyl groups and fused (cycloalkylaryl)alkyl groups such as 4-ethyl-indanyl. Representative substituted aralkyl groups can be substituted one or more times with substituents such as those listed above.

Heterocyclyl groups include aromatic (also referred to as heteroaryl) and non-aromatic ring compounds containing 3 or more ring members, of which one or more is a heteroatom such as, but not limited to, N, O, and S. In some embodiments, heterocyclyl groups include 3 to 20 ring members, whereas other such groups have 3 to 6, 3 to 10, 3 to 12, or 3 to 15 ring members. Heterocyclyl groups encompass unsaturated, partially saturated and saturated ring systems, such as, for example, imidazolyl, imidazolinyl and imidazolidinyl groups. The phrase "heterocyclyl group" includes fused ring species including those comprising fused aromatic and non-aromatic groups, such as, for example, benzotriazolyl, 2,3-dihydrobenzo[1,4]dioxinyl, and benzo[1,3]dioxolyl. The phrase also includes bridged polycyclic ring systems containing a heteroatom such as, but not limited to, quinuclidyl. However, the phrase does not include heterocyclyl groups that have other groups, such as alkyl, oxo or halo groups, bonded to one of the ring members. Rather, these are referred to as "substituted heterocyclyl groups". Heterocyclyl groups include, but are not limited to, aziridinyl, azetidinyl, pyrrolidinyl, imidazolidinyl, pyrazolidinyl, thiazolidinyl, tetrahydrothiophenyl, tetrahydrofuranyl, dioxolyl, furanyl, thiophenyl, pyrrolyl, pyrrolinyl, imidazolyl, imidazolinyl, pyrazolyl, pyrazolinyl, triazolyl, tetrazolyl, oxazolyl, isoxazolyl, thiazolyl, thiazolinyl, isothiazolyl, thiadiazolyl, oxadiazolyl, piperidyl, piperazinyl, morpholinyl, thiomorpholinyl, tetrahydropyranyl, tetrahydrothiopyranyl, oxathiane, dioxyl, dithianyl, pyranyl, pyridyl, pyrimidinyl, pyridazinyl, pyrazinyl, triazinyl, dihydropyridyl, dihydrodithiinyl, dihydrodithionyl, homopiperazinyl, quinuclidyl, indolyl, indolinyl, isoindolyl, azaindolyl(pyrrolopyridyl), indazolyl, indolizinyl, benzotriazolyl, benzimidazolyl, benzofuranyl, benzothiophenyl, benzthiazolyl, benzoxadiazolyl, benzoxazinyl, benzodithiinyl, benzoxathiinyl, benzothiazinyl, benzoxazolyl, benzothiazolyl, benzothiadiazolyl, benzo[1,3]dioxolyl, pyrazolopyridyl, imidazopyridyl(azabenzimidazolyl), triazolopyridyl, isoxazolopyridyl, purinyl, xanthinyl, adeninyl, guaninyl, quinolinyl, isoquinolinyl, quinolizinyl, quinoxalinyl, quinazolinyl, cinnolinyl, phthalazinyl, naphthyridinyl, pteridinyl, thianaphthalenyl, dihydrobenzothiazinyl, dihydrobenzofuranyl, dihydroindolyl, dihydrobenzodioxinyl, tetrahydroindolyl, tetrahydroindazolyl, tetrahydrobenzimidazolyl, tetrahydrobenzotriazolyl, tetrahydropyrrolopyridyl, tetrahydropyrazolopyridyl, tetrahydroimidazopyridyl, tetrahydrotriazolopyridyl, and tetrahydroquinolinyl groups. Representative substituted heterocyclyl groups can be mono-substituted or substituted more than once, such as, but not limited to, pyridyl or morpholinyl groups, which are 2-, 3-, 4-, 5-, or 6-substituted, or disubstituted with various substituents such as those listed above.

Heteroaryl groups are aromatic ring compounds containing 5 or more ring members, of which, one or more is a heteroatom such as, but not limited to, N, O, and S. Heteroaryl groups include, but are not limited to, groups such as pyrrolyl, pyrazolyl, triazolyl, tetrazolyl, oxazolyl, isoxazolyl, thiazolyl, pyridyl, pyridazinyl, pyrimidinyl, pyrazinyl, thiophenyl, benzothiophenyl, furanyl, benzofuranyl, indolyl, azaindolyl(pyrrolopyridyl), indazolyl, benzimidazolyl, imidazopyridyl(azabenzimidazolyl), pyrazolopyridyl, triazolopyridyl, benzotriazolyl, benzoxazolyl, benzothiazolyl, benzothiadiazolyl, imidazopyridyl, isoxazolopyridyl, thianaphthalenyl, purinyl, xanthinyl, adeninyl, guaninyl, quinolinyl, isoquinolinyl, tetrahydroquinolinyl, quinoxalinyl, and quinazolinyl groups. Although the phrase "heteroaryl groups" includes fused ring compounds such as indolyl and 2,3-dihydro indolyl, the phrase does not include heteroaryl groups that have other groups bonded to one of the ring members, such as alkyl groups. Rather, heteroaryl groups with such substitution are referred to as "substituted heteroaryl groups." Representative substituted heteroaryl groups can be substituted one or more times with various substituents such as those listed above.

Synthesis of Quinolines

Methods of making compounds of formula I are well known in the art. For example, the Skraup synthesis in which a primary aromatic amine reacts with glycerol, sulfuric acid and an oxidizing agent, is a well-known method for preparing quinolines. For quinolines with substituents in the hetero ring, a modified Skraup synthesis may be employed, substituting acrolein or a vinyl ketone for glycerol. Suitable methods are described in, for example, Ginsburg, *Synthesis of Heterocyclic Amines* in Concerning Amines (Elsevier, 1967). Other techniques described in the literature and known to a person of ordinary skill in the art may be employed to produce the quinolines as described herein.

Formulations

As hyperpigmentation is a skin disorder that may be treated with topical creams, ointments, lotions, patches, microneedling, or the like, the compounds of Formulas I may be formulated as topical treatments in the disclosed embodiments. In some embodiments, the compounds of formula I may be combined with a pharmaceutically acceptable carrier for cutaneous topical application. The choice of pharmaceutically acceptable carrier, excipient or diluent may be selected based on the formulation and intended route of administration, as well as standard pharmaceutical practice. Such compositions may comprise agents that may aid, regulate, release or increase entry into the body compartment, tissue, intracellular or intranuclear target site, such as binder, lubricants, suspending agents, coating agents, solubilizing agents or other agents, including those that may provide for the sustained release of the pharmaceutical formation to obtain prolonged exposure and action. The term "sustained release" refers to pharmaceutical formulations from which the tyrosinase inhibitor is released at a slow rate allowing for a longer period of exposure at active concentrations.

The compounds of formula I may, as appropriate, be used as a free acid or as a pharmaceutically acceptable salt. As used herein, the term "pharmaceutically acceptable salt" refers to those salts which are, within the scope of sound medical judgment, suitable for use in contact with the tissues of humans without undue toxicity, irritation, allergic response and the like, and are commensurate with a reasonable benefit/risk ratio. Suitable pharmaceutically acceptable salts are well known in the art. See, e.g., Berge et al. *J. Pharmaceutical Sciences,* 1977, 66:1-19. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, alkyl having from 1 to 6 carbon atoms, sulfonate and aryl sulfonate.

The compounds of formula I may also be provided in the form of a pharmaceutically acceptable derivative or prodrug, which is any pharmaceutically acceptable salt, ester, salt of an ester, or other derivative of the compound of formula I, which, upon administration to a recipient, is capable of providing (directly or indirectly) the compound(s) of formula I. Suitable prodrugs include, for example, esters and amides that are hydrolytically labile in vivo.

In one aspect, the embodiments disclosed herein provide a pharmaceutical composition comprising a compound of formula I together with a pharmaceutically suitable carrier, excipient or additive. The pharmaceutical composition may also further include one or more additional dermatological agents. Suitable dermatological agents include sunscreen or exfoliant compounds, which may have additional properties advantageous to treating a hyperpigmentary disorder. Exfoliant compounds increase the rate of turnover of the surface layer(s) of the skin, thereby increasing the rate of removal of overly or undesirably pigmented skin cells. Compounds with sunscreen activity block the increase in melanin production that ordinarily results from exposure to UV radiation from the sun.

Exfoliants

Exfoliants that can be used in the compositions as described herein can be either manual or chemical. Manual skin exfoliants are mild abrasives such as micro-bead facial scrubs, crushed apricot kernels or almond shells, or pumice. Mechanical friction with abrasives exfoliates the outer corneocytes that comprise the stratum corneum layer.

More advantageously, the exfoliant(s) used are chemical, and may include enzymatic agents. Chemical exfoliant agents are well known in the art. Examples include salicylic acid, glycolic acid, fruit enzymes, citric acid, and malic acid. Chemical exfoliation may involve the use of products containing $\alpha$-hydroxy acids (AHA) or $\beta$-hydroxy acids (BHAs) or keratolytic enzymes that dissociate the top layer of dead skin cells. The main enzymes used in skin exfoliation are papain from papaya, bromelain from pineapple and an enzyme from pumpkin. Papain and bromelain are proteolytic enzymes that stimulate exfoliation by digesting intercorneocyte cohesion. Additional exfoliants that can be used include herbal exfoliants, reviewed in Packianathan and Kandasamy, *Functional Plant Science and Biotechnology* 2009, 5:94-97.

Sunscreens

Sunscreen compounds can protect the skin from UVA and/or UVB radiation and therefore reduce or prevent generation of additional melanin pigmentation.

UVB filters useful in the compositions described herein may be oil-soluble or water-soluble. Oil-soluble UVB filters include, for example: derivatives of 3-benzylidene camphor, preferably 3-(4-methylbenzylidene)camphor; derivatives of 4-aminobenzoic acid, preferably 2-(ethylhexyl)4-dimethylamino-benzoate, amyl 4-(dimethylamino)-benzoate; esters of cinnamic acid, preferably (2-ethylhexyl)4-methoxy cinnamate, isopentyl 4-methoxy cinnamate; esters of salicylic acid, preferably (2-ethylhexyl)salicylicate, (4-isopropylbenzyl)salicylicate, homomenthyl salicylicate; derivatives of benzophenone, preferably 2-hydroxy-4-methoxybenzophenone, 2-hydroxy-4-methoxy-4'-methylbenzophenone, 2,2'-dihydroxy-4-methoxybenzophenone; esters of benzalmalonic acid, preferably di(2-ethylhexyl) 4-methoxybenzalmalonate; and 2,4,6-trianilino-(p-carbo-2'-ethyl-1'-hexyloxy)-1,3,5-triazine.

Water-soluble UVB filters include, for example: 2-phenylbenzimidazole-5-sulfonic acid and its salts, such as its sodium-, potassium-, or its triethanol ammonium salts; sulfonic acid derivatives of benzophenones, preferably, 2-hydroxy-4-methoxybenzophenone-5-sulfonic acid and its salts; and sulfonic acid derivatives of 3-benzylidene camphor, such as, for example, 4-(2-oxo-3-bornylidene-methyl) benzenesulfonic acid, 2-methyl-5-(2-oxo-3-bornylidenemethyl)sulfonic acid and their salts. UVB filters are well known in the art and the skilled artisan will appreciate that the filters described above are merely illustrative and are not intended to be limiting.

UVA filters can include, for example, derivatives of dibenzoylmethane, in particular 1-(4'-tert-butylphenyl)-3-(4'-methoxyphenyl)propane-1,3-dione and 1-phenyl-3-(4'-isopropylphenyl)propane-1,3-dione. UVB filters are well known in the art and the skilled artisan will appreciate that the filters described above are merely illustrative and are not intended to be limiting. The total amount of the UV filter substances may be, for example, from 0.1 wt. % to 30 wt. %, advantageously 0.5 wt. % to 10 wt. %, more advantageously 1.0 to 6.0 wt. % based on the total weight of the preparations.

One of ordinary skill in the art will recognize that a therapeutically effective amount of one of more compounds according to the disclosed embodiments will vary with the condition to be treated, its severity, the treatment regimen to be employed, the pharmacokinetics of the agent used, as well as the individual being treated.

To prepare the pharmaceutical compositions according to the disclosed embodiments, a therapeutically effective amount of one or more of the compounds according to the disclosed embodiments are preferably intimately admixed with a pharmaceutically acceptable carrier according to conventional pharmaceutical compounding techniques to produce a dose. A carrier may take a wide variety of topical forms depending on the form of preparation desired for administration, e.g., including gels, creams ointments, lotions, transdermal patches, masks, solutions, washes and cleansers, microneedling, and time released preparations, among others.

In some embodiments, the active compound is included in the pharmaceutically acceptable carrier or diluent in an amount sufficient to deliver to a patient a therapeutically effective amount for the desired indication, without causing serious toxic effects in the patient treated.

Solutions or suspensions used for intradermal or topical application can include the following components: a sterile diluent such as water, saline solution, fixed oils, polyethylene glycols, glycerin, propylene glycol or other synthetic solvents; antibacterial agents such as benzyl alcohol or methyl parabens; antioxidants such as ascorbic acid or sodium bisulfite; chelating agents such as ethylenediaminetetraacetic acid (EDTA); buffers such as acetates, citrates or phosphates and agents for the adjustment of tonicity such as sodium chloride or dextrose. Other compounds suitable for use in compositions for hyperpigmentation treatments include steroids, retinoids, absorption enhancers, and anti-inflammatory agents.

In some embodiments, the active compounds are prepared with carriers that will protect the compound against rapid elimination from the body, such as a controlled release formulation, including implants or patches. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art.

A skilled artisan will recognize some dosage forms, such as, e.g., transdermal patches, can be formulated to provide slow or controlled release of the active ingredient.

In some embodiments, formulations suitable for topical administration to the skin may be presented as ointments, creams, gels and pastes comprising the ingredient to be administered in a pharmaceutical acceptable carrier. A preferred topical delivery system is a patch containing the ingredient to be administered.

In certain embodiments, the prodrug form of the compounds may be preferred. One of ordinary skill in the art will recognize how to readily modify the present compounds to prodrug forms to facilitate delivery of active compounds to a targeted site within the host organism or patient. The routineer also will take advantage of favorable pharmacokinetic parameters of the prodrug forms, where applicable, in delivering the present compounds to a targeted site within the host organism or patient to maximize the intended effect of the compound.

In some embodiments, the preferred prodrugs include derivatives where a group, which enhances aqueous solubility or active transport through a barrier such as skin, is appended to the structure of formula I. See, e.g., Alexander, J. et al. Journal of Medicinal Chemistry 1988, 31, 318-322; Bundgaard, H. Design of Prodrugs; Elsevier: Amsterdam, 1985; pp 1-92; Bundgaard, H.; Nielsen, N. M. *Journal of Medicinal Chemistry* 1987, 30:451-454; Bundgaard, H. *A Textbook of Drug Design and Development*; Harwood Academic Publ.: Switzerland, 1991; pp 113-191; Digenis, G. A. et al. *Handbook of Experimental Pharmacology* 1975, 28:86-112; Friis, G. J.; Bundgaard, H. *A Textbook of Drug Design and Development*; 2 ed.; Overseas Publ.: Amsterdam, 1996; pp 351-385; Pitman, I. H. *Medicinal Research Reviews* 1981, 1:189-214. The prodrug forms may be active themselves, or may be those, such that when metabolized, after administration provide the active therapeutic agent in vivo.

Pharmaceutically acceptable salt forms may be the preferred chemical form of compounds according to the disclosed embodiments for inclusion in pharmaceutical compositions.

The concentration of active compound in the drug composition will depend on absorption, distribution, inactivation, and excretion rates of the drug as well as other factors known to those of skill in the art. It is to be noted that dosage values will also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed composition. The active ingredient may be administered once, or may be divided into a number of smaller doses to be administered at varying intervals of time.

In certain embodiments, the pharmaceutical formulation is administered once daily; in other embodiments, the compound is administered twice daily; in yet other embodiments, the compound is administered once every two days, once every three days, once every four days, once every five days, once every six days, once every seven days, once every two weeks, once every three weeks, once every four weeks, once every two months, once every six months, or once per year. The dosing interval can be adjusted according to the needs of individual patients. For longer intervals of administration, extended release or depot formulations can be used.

Methods of Treatment

Methods of treating hyperpigmentation with such topical treatments include applying the topical pharmaceutical formulation to a portion of skin that is affected by or that is at risk from hyperpigmentation. The treatment regimen of such a method should be determined by one of skill in the art, or the affected subject's clinician. The topical treatment may be used daily, weekly, monthly or at other prescribed intervals; the topical treatment also may be used more than once a day, e.g., the compounds of formula may be administered for time periods exceeding two weeks, three weeks, one month, two months, three months, four months, five months, six months, one year, two years, three years, four years, or five years, ten years, or fifteen years; or for example, any time period range in days, months or years in which the low end of the range is any time period between 14 days and 15 years and the upper end of the range is between 15 days and 20 years (e.g., 4 weeks and 15 years, 6 months and 20 years). In some cases, it may be advantageous for the compounds of the disclosed embodiments to be administered for the remainder of the patient's life.

In preferred embodiments, the patient is monitored to check the progression of the disease or disorder, and the dose is adjusted accordingly.

In preferred embodiments, treatment is effective for at least two weeks, three weeks, one month, two months, three months, four months, five months, six months, one year, two years, three years, four years, or five years, ten years, fifteen years, twenty years, or for the remainder of the subject's life.

The amounts and dosage regimens administered to a subject will depend on a number of factors, such as the mode of administration, the nature of the condition being treated, the body weight of the subject being treated and the judgment of the prescribing physician.

The amount of compound included within therapeutically active formulations according to the disclosed embodiments is an effective amount for treating the condition.

In general, a therapeutically effective amount of the present preferred compound in dosage form usually ranges from less than about 0.025 mg/kg patient body weight to about 2.5 g/kg patient body weight on a per day or other time period basis, regardless if those amounts are delivered in a single dose or apportioned over multiple doses in the specified period. In the most preferred embodiments, pharmaceutical formulations according to the present invention are administered in a suitable carrier in amounts ranging from about 1 mg/kg to about 100 mg/kg per day or per other period, regardless if those amounts are delivered in a single dose or apportioned over multiple doses in the specified period. The dosing and timing of dosing will depend on the condition being treated, the particular compound, and other clinical factors such as weight and condition of the patient, and the manner of administration of the formulation, among other things.

Thus, in the disclosed embodiments, a therapeutically effective amount of the present preferred pharmaceutical formulation in dosage form is, based on a daily or other period basis, usually less than about 0.010 mg/kg body weight, less than about 0.025 mg/kg, less than about 0.050 mg/kg, less than about 0.075 mg/kg, less than about 0.100 mg/kg, less than about 0.15 mg/kg, less than about 0.20 mg/kg, less than about 0.25 mg/kg, less than about 0.30 mg/kg, less than about 0.35 mg/kg, less than about 0.40 mg/kg, less than about 0.45 mg/kg, less than about 0.50 mg/kg, less than about 0.55 mg/kg, less than about 0.60 mg/kg, less than about 0.65 mg/kg, less than about 0.70 mg/kg, less than about 0.75 mg/kg, less than about 0.80 mg/kg, less than about 0.85 mg/kg, less than about 0.90 mg/kg, less than about 0.95 mg/kg, less than about 1.0 mg/kg, less than about 2.0 mg/kg, less than about 3.0 mg/kg, less than about 4.0 mg/kg, less than about 5.0 mg/kg, less than about 6.0 mg/kg, less than about 7.0 mg/kg, less than about 8.0 mg/kg, less than about 9.0 mg/kg, less than about 10.0 mg/kg, less than about 11.0 mg/kg, less than about 12.0 mg/kg, less than about 13.0 mg/kg, less than about 14.0 mg/kg, less than about 15.0 mg/kg, less than about 16.0 mg/kg, less than about 17.0 mg/kg, less than about 18.0 mg/kg, less than about 19.0 mg/kg, less than about 20.0 mg/kg, less than about 25.0 mg/kg, less than about 30.0 mg/kg, less than about 35.0 mg/kg, less than about 40.0 mg/kg, less than about 45.0 mg/kg, less than about 50.0 mg/kg, less than about 55.0 mg/kg, less than about 60.0 mg/kg, less than about 65.0 mg/kg, less than about 70.0 mg/kg, less than about 75.0 mg/kg, less than about 80.0 mg/kg, less than about 85.0 mg/kg, less than about 90.0 mg/kg, less than about 95.0 mg/kg, less than about 100 mg/kg, less than about 120.0 mg/kg, less than about 140.0 mg/kg, less than about 160.0 mg/kg, less than about 180.0 mg/kg, less than about 200.0 mg/kg, less than about 250.0 mg/kg, less than about 300.0 mg/kg, less than about 350.0 mg/kg, less than about 400.0 mg/kg, less than about 600.0 mg/kg, less than about 800.0 mg/kg, less than about 1.0 g/kg, less than about 1.5 g/kg, less than about 2.0 g/kg, less than about 2.5 g/kg, less than about 2.75 g/kg, ranges between about 0.10 mg/kg to about 1.25 mg/kg, ranges between about 0.10 mg/kg to about 0.50 mg/kg, ranges between about 0.20 mg/kg to about 0.40 mg/kg, ranges between about 0.20 mg/kg to about 0.60 mg/kg, ranges between about 0.30 mg/kg to about 0.70 mg/kg, ranges between about 0.40 mg/kg to about 0.80 mg/kg, ranges between about 0.50 mg/kg to about 0.90 mg/kg, ranges between about 0.60 mg/kg to about 1.0 mg/kg, ranges between about 0.90 mg/kg to about 1.10 mg/kg, ranges between about 1.00 mg/kg to about 1.30 mg/kg, ranges between about 1.10 mg/kg to about 1.5 mg/kg, ranges between about 1.25 mg/kg to about 1.75 mg/kg, ranges between about 1.5 mg/kg to about 2.0 mg/kg, ranges between about 1.75 mg/kg to about 2.25 mg/kg, ranges between about 2.0 mg/kg to about 2.5 mg/kg, ranges between about 2.0 mg/kg to about 5.0 mg/kg, ranges between about 3.0 mg/kg to about 7.0 mg/kg, ranges between about 5.0 mg/kg to about 10 mg/kg, ranges between about 10.0 mg/kg to about 20 mg/kg, ranges between about 20.0 mg/kg to about 30.0 mg/kg, ranges between about 30.0 mg/kg to about 40 mg/kg, ranges between about 40.0 mg/kg to about 50.0 mg/kg, ranges between about 50.0 mg/kg to about 60.0 mg/kg, ranges between about 60.0 mg/kg to about 70.0 mg/kg, ranges between about 70.0 mg/kg to about 80.0 mg/kg, ranges between about 80.0 mg/kg to about 90.0 mg/kg, ranges between about 90.0 mg/kg to about 100.0 mg/kg, ranges between about 100.0 mg/kg to about 110.0 mg/kg, ranges between about 110.0 mg/kg to about 120.0 mg/kg, ranges between about 120.0 mg/kg to about 130.0 mg/kg, ranges between about 130.0 mg/kg to about 140.0 mg/kg, ranges between about 140.0 mg/kg to about 150.0 mg/kg, ranges between about 150.0 mg/kg to about 160.0 mg/kg, ranges between about 160.0 mg/kg to about 170.0 mg/kg, ranges between about 170.0 mg/kg to about 180.0 mg/kg, ranges between about 180.0 mg/kg to about 190.0 mg/kg ranges between about 190.0 mg/kg to about 200.0 mg/kg, ranges between about 200.0 mg/kg to about 250.0 mg/kg, ranges between about 250.0 mg/kg to about 300.0 mg/kg, ranges between about 300.0 mg/kg to about 350.0 mg/kg, ranges between about 350.0 mg/kg to about 400.0 mg/kg, ranges between about 400.0 mg/kg to about 450.0 mg/kg, ranges between about 450.0 mg/kg to about 500.0 mg/kg, ranges between about 500.0 mg/kg to about 550.0 mg/kg, ranges between about 550.0 mg/kg to about 600.0 mg/kg, ranges between about 600.0 mg/kg to about 650.0 mg/kg, ranges between about 650.0 mg/kg to about 700.0 mg/kg, ranges between about 700.0 mg/kg to about 750.0 mg/kg, ranges between about 750.0 mg/kg to about 800.0 mg/kg, ranges between about 800.0 mg/kg to about 850.0 mg/kg, ranges between about 850.0 mg/kg to about 900.0 mg/kg, ranges between about 900.0 mg/kg to about 950.0 mg/kg, ranges between about 950.0 mg/kg to about 1.0 g/kg, ranges between about 1.0 g/kg to about 1.2 g/kg, ranges between about 1.2 g/kg to about 1.4 g/kg, ranges between about 1.4 g/kg to about 1.6 g/kg, ranges between about 1.6 g/kg to about 1.8 g/kg, ranges between about 1.8 g/kg to about 2.0 g/kg, ranges between about 2.0 g/kg to about 2.25 g/kg, ranges between about 2.25 g/kg to about 2.5 g/kg, ranges from about 2.5 g/kg to about 2.75 g/kg, ranges from about 2.75 g/kg to about 3.0 g/kg of body weight. Typically, a dermatologist will determine the actual dosage most suitable for an individual subject, and it will vary by patient, and a variety of patient and other characteristics.

All ranges and ratios discussed here can and necessarily do describe all subranges and subratios therein for all purposes, and all such subranges and subratios also form part and parcel of the disclosed embodiments. Any listed range or ratio can be easily recognized as sufficiently describing and enabling the same range or ratio being broken down into at least equal halves, thirds, quarters, fifths, tenths, etc. As a non-limiting example, each range or ratio discussed herein can be readily broken down into a lower third, middle third and upper third, etc.

The embodiments disclosed of pharmaceutical formulations may be used alone or in combination with other treatments or components of treatments for other dermatological or nondermatological disorders.

The disclosed embodiments will be better understood by reference to the following examples which are intended for purposes of illustration and are not intended to be interpreted in any way to limit the scope of the appended claims.

The word "exemplary" is used herein to mean "serving as an example, instance, or illustration." Any embodiment described herein as "exemplary" is not necessarily to be construed as preferred or advantageous over other embodiments.

It is to be understood that the singular forms "a," "an," and "the" include the plural forms unless the context clearly dictates otherwise, e.g., reference to "a dermatologically active compound" includes reference to one or more such compounds.

Similarly, it should be appreciated that in the above description of embodiments, various features are sometimes grouped together in a single embodiment, Figure, or description thereof for the purpose of streamlining the disclosure. This method of disclosure, however, is not to be interpreted as reflecting an intention that any claim in this or any application claiming priority to this application require more features than those expressly recited in that claim. Rather, as the following claims reflect, inventive aspects lie in a combination of fewer than all features of any single foregoing disclosed embodiment. Thus, the claims following this Detailed Description are hereby expressly incorporated into this Detailed Description, with each claim standing on its own as a separate embodiment. This disclosure includes all permutations of the independent claims with their dependent claims. Recitation in the claims of the term "first" with respect to a feature or element does not necessarily imply the existence of a second or additional such feature or element. Elements recited in means-plus-function format are intended to be construed in accordance with 35 U.S.C. § 112 ¶6. It will be apparently to those having skill in the art that changes may be made to the details of the above-described embodiments without departing from the underlying principles of the disclosed embodiments.

While specific embodiments and application of the disclosed embodiments have been illustrated and described, it is to be understood that the disclosed embodiments are not limited to the precise configuration and components disclosed herein. Various modifications, changes, and variations, which will be apparent to those skilled in the art may be made in the arrangement, operation, and details of the methods and systems of the embodiments disclosed herein, including those of the appended claims. Finally, various features of the disclosed embodiments herein may be combined to provide additional configurations which fall within the scope of the disclosed embodiments. The following examples are intended to illustrate the kinetic measures and the efficacy of inhibitory compounds tested, including those in the disclosed embodiments.

EXAMPLES

All drugs and analogs were obtained from commercial suppliers.

The identification of potential inhibitors was pursued through a database search of approved drugs for those whose structure contained a phenol moiety. Lower molecular weight molecules were identified that would be of similar size to tyrosine and would therefore fit in the tyrosinase active site. A substructure search of the Cheminfo database of FDA-approved drugs identified the class of antibiotics, aminoquinolines (FIG. 3 (a) Table).

Example 1

Kinetic Assays

Enzyme activity was measured using the fluorescent substrate PAP-AMC. Germanas, J. P., et al., *Bioorg. Med. Chem. Lett.* 2007, 17, 6871-6875. Fluorescence spectroscopy was carried out on a Carey Eclipse spectrophotometer. Fluorescence intensity was measured at 6-second intervals in quartz cuvettes kept at 37° C. Prospective inhibitory compounds were tested to ensure they had no fluorescent activity at the wavelengths used to reduce spectrophotometric artifacts. FIG. 3 (b) depicts the inhibition of tyrosinase activity by a variety of these hydroxyquinoline drugs. In vitro fluorescence assays using mushroom tyrosinase (Worthington Biochemicals) were performed in 50 mM sodium phosphate buffer, pH 7.4 with the fluorescent tyrosinase substrate, PAP-AMC (Biovision). Varying concentrations of inhibitors were used as indicated. Data represent the mean±SD of three independent experiments.

Enzyme Kinetic Measurements

In a 3 mL cuvette, buffer (total volume of 2.0 mL of 50 mM phosphate, pH 7.4), and DMSO (total DMSO in assay of 0.050 mL) were heated to 37° C. for 2 min. Enzyme solution (final concentration of 0.25 mg/mL), and L-DOPA (0.002 mL of 5 mM) were added. After 5 minute incubation, inhibitor was added as a solution in DMSO. After an additional 2 minute incubation, a DMSO solution of PAP-AMC (0.02 mL of 1 mM solution) was added and, after thoroughly mixing, the reaction was monitored by fluorescence ($\lambda$ excitation=350 nm; $\lambda$ emission=440 nm). Initial rates were calculated using the slope of the curve for the first ca. 10% of the reaction. The first 1 min of the reaction were not used owing to the usual induction period observed with tyrosinase. Inhibition assays were performed in triplicate trials. Non-linear regression and curve fitting were done using Prism software (Graphpad Inc). FIG. 4 (a) depicts the kinetics of tyrosinase inhibition by nitroxoline at the µM concentrations as indicated. The experiment was performed in triplicate at pH 7.4 and data were plotted according to Lineweaver-Burk. Data represent the mean±SD of three independent experiments.

Example 2

Assessment of Reversibility

To assess reversibility of enzyme inhibition, a reaction mixture containing 5 µM inhibitor was placed into Amicon Ultra centrifugal filters (10 K MWCO), concentrated at 4000 rpm for 10 minutes, followed by dilution with sodium phosphate buffer for a total of three cycles. If reconstitution of enzyme activity was being evaluated, exogenous copper sulfate was added to the remaining solution to a final concentration of 0.1 mM. Then fresh L-DOPA and PAP-AMC substrate was added and fluorescence change measured as previously described. The recovery of activity with exogenous copper strongly suggests that hydroxyquinolines inhibit tyrosinase by chelating the copper atom in the enzyme active site, and, at higher concentrations, actually extrude the metal ion, forming a bis-(hydroxyquinoline) copper complex. FIG. 4(b) depicts the enzymatic activity of tyrosinase after ultrafiltration of nitroxoline. Bars represent, from left to right, percentage of initial activity without inhibitor; with 5 µM inhibitor before ultrafiltration; with 5 µM inhibitor after ultrafiltration and 30 minute incubation with 0.1 mM final concentration copper sulfate; 10 minute incubation with 0.1 mM final concentration copper sulfate; and after ultrafiltration and no exogenous copper sulfate.

Example 3

Inhibition of Melanin Production in Human Melanoma Cells

To assess melanogenesis inhibition within cells, the human melanoma MNT-1 cell line (CRL-3450 from ATCC), cultured and divided according to the recommended protocol, was subjected to varying concentrations of chloroxine (2) and the other hydroxyquinoline drugs. The MNT-1 cell line was chosen because it was previously used successfully for quantifying melanin synthesis (Hah et al., 2012). Frozen stocks ($3.8 \times 10^6$ cells) of cells were thawed in a 37° C. water bath, then plated into three 10-cm plates containing 10 mL of MDEM+10% fetal bovine serum and 100 µL of 100× Penicillin/Streptomycin. When the cells became confluent, medium was aspirated, cells were rinsed with sterile phosphate-buffered saline (PBS), and then treated with 1 mL of 0.25% trypsin with 0.02% EDTA at 37° C. for 3 min. When the cells became loose, 4 mL of medium was added to neutralize the trypsin. FIG. 5 depicts the inhibition of melanin production in MNT-1 cells by chloroxine, an inhibitor of tyrosinase, at concentrations indicated. Cells were incubated with chloroxine for 3 days and then harvested, with melanin quantified after cell lysis, measuring absorbance at 405 nm.

Example 4

Assessment of Inhibition of Melanin Synthesis

To assess inhibition of melanin synthesis, freshly passaged cells were seeded into six-well plates at a density of 30,000 cells per well, cultured in MDEM medium and supplemented with 10% fetal bovine serum at 37° C. in a humidified atmosphere of 5% $CO_2$ in air. Inhibitor compounds were added in a DMSO stock solution to final concentrations of 20 to 200 µM. The well-characterized tyrosinase inhibitor phenylthiourea (PTU) was used as a positive control, and DMSO, a solvent (as a negative control). After three days the cells were washed with phosphate-buffered saline (PBS) and dissolved in 250 µL of 1 N NaOH for one hour at 80° C. and transferred to 96-well plates. After a specified incubation time, the cells were lysed and melanin content was measured spectrophotometrically (at a wavelength of 405 nm). Percent inhibition for each concentration of each inhibitor compound was calculated according to the equation below Percent inhibition=$[1-(A_{cmpd}-A_p)/(A_n-A_p)] \times 100$ Where $A_{cmpd}$ is the absorbance value for the test compound, and $A_p$ and $A_n$ are the absorbance values of the positive and negative controls, respectively. FIG. 6 depicts the reduction in melanin biosynthesis in MNT-1 cells by chloroxine, relative to the positive control phenylthiourea (PTU), a tyrosinase inhibitor commonly used as a melanin synthesis blocker. Other hydroxyquinoline drugs caused different effects in the MNT-1 cell line. At higher concentrations, the iodo-substituted compounds clioquinol (3) and iodoquinol (4) were toxic, with decreased cell counts in the viability assay. In contrast nitroxoline (1) (not shown) and chloroxine (2), shown in FIG. 6, were not toxic. Chloroxine displayed a dose-dependent ability to block melanin production within MNT-1 cells, FIG. 5. The $IC_{50}$ value for blocking melanin synthesis was estimated at ~1.5 µmol/L.

Example 5

Molecular Modeling

Overlay and visualization of protein-inhibitor complexes were assessed with PyMOL version 2.5.0. Structures of hydroxyquinolines were obtained from PubChem for the modeling process. The crystal structure of *Agaricus bisporus* (mushroom) tyrosinase complexed with the inhibitor tropolone (PDB: 2Y9X) was retrieved from the Protein DataBank (www.rcsb.org). FIG. 7 (a) is a diagram showing the positions of metal-binding lone pairs of electrons in the structures of (i) nitroxoline, the simplest 8-hydroxyquinoline drug; and (ii) kojic acid. FIG. 7 (b) is an illustration representing chloroxine positioned within the active site of A *bisporus* tyrosinase when overlayed with the analogous atoms of tropolone in the tyrosinase-tropolone co-crystal structure. Compared with the structure of kojic acid, carbon atoms 2, 3 and 4 of the 8-hydroxyquinoline core structure may potentially create adverse steric interactions when the inhibitor binds to tyrosinase in the same relative position as in the co-crystal structure. But, as evidenced in the overlay in FIG. 7 (*b*), such adverse interactions do not occur; in fact, beneficial hydrophobic interactions with the isopropyl side chain group of Val283, and edge-to-face aromatic interactions with the phenyl side chain of Phe264.

The description provided herein is provided to assist in a comprehensive understanding of various embodiments of the disclosure as defined by the claims and their equivalents. It includes various specific details to assist in that understanding but these are to be regarded as exemplary. Accordingly, those of ordinary skill in the art will recognize that various changes and modifications of the various embodiments described herein can be made without departing from the scope and spirit of the disclosure. In addition, descriptions of well-known functions and constructions may be omitted for clarity and conciseness.

What is claimed is:

1. A method of treating a pigmentary disorder, comprising administering to a patient suffering from said pigmentary disorder an effective amount of a dermatologically acceptable pharmaceutical composition comprising an effective amount of a tyrosinase inhibitor of formula (I),

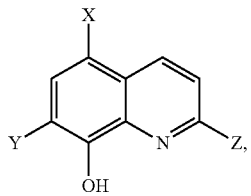

(I)

wherein X is $NO_2$, Cl, or I,

Y is H, Cl, or I, wherein when X is Cl, Y is I, and Z is H, and wherein said composition optionally comprises an effective amount of a second dermatologically active compound.

2. The method according to claim 1, wherein said second dermatologically active compound is present and is selected from the group consisting of a retinoid, a sunscreen, an exfoliant, and an anti-inflammatory agent.

3. The method according to claim 1, wherein X is $NO_2$ and Y is H.

4. The method according to claim 1, wherein X is Cl.

5. The method according to claim 1, wherein X and Y are I.

6. The method according to claim 1, wherein said pigmentary disorder is selected from the group consisting of melasma, chloasma, lentigines, senile lentigo, an irregular hyperpigmentation related to photoaging, freckles, a post-inflammatory hyperpigmentation due to an abrasion, a burn, a scar, dermatosis, a contact allergy and naevi.

7. The method according to claim 2, wherein the second dermatologically active compound is a retinoid.

8. The method according to claim 2, wherein the second dermatologically active compound is a sunscreen.

9. The method according to claim 2, wherein the second dermatologically active compound is an anti-inflammatory agent.

10. The method according to claim 6, wherein said pigmentary disorder is melasma.

11. The method according to claim 6, wherein said pigmentary disorder is lentigo.

12. The method according to claim 6, wherein said pigmentary disorder is post-inflammatory hyperpigmentation.

* * * * *